US008968753B2

(12) United States Patent
Terracciano et al.

(10) Patent No.: US 8,968,753 B2
(45) Date of Patent: *Mar. 3, 2015

(54) CEFTOLOZANE-TAZOBACTAM PHARMACEUTICAL COMPOSITIONS

(71) Applicant: Calixa Therapeutics, Inc., Lexington, MA (US)

(72) Inventors: Joseph Terracciano, Concord, MA (US); Nicole Miller Damour, Belmont, MA (US); Chun Jiang, Hillsborough, CA (US); Giovanni Fogliato, Barzana (IT); Giuseppe Alessandro Donadelli, Casalpusterlengo (IT); Dario Resemini, Milan (IT)

(73) Assignee: Calixa Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/285,185

(22) Filed: May 22, 2014

(65) Prior Publication Data

US 2014/0274998 A1    Sep. 18, 2014

Related U.S. Application Data

(63) Continuation of application No. 14/214,212, filed on Mar. 14, 2014, now abandoned.

(60) Provisional application No. 61/793,007, filed on Mar. 15, 2013, provisional application No. 61/792,092, filed on Mar. 15, 2013.

(51) Int. Cl.
| | |
|---|---|
| *A61K 9/00* | (2006.01) |
| *A61K 31/43* | (2006.01) |
| *A61K 31/545* | (2006.01) |
| *A61K 9/19* | (2006.01) |
| *A61K 31/546* | (2006.01) |
| *A61K 31/431* | (2006.01) |
| *A61K 47/02* | (2006.01) |
| *A61K 47/12* | (2006.01) |
| *A61K 47/18* | (2006.01) |

(52) U.S. Cl.
CPC ............... *A61K 9/19* (2013.01); *A61K 31/546* (2013.01); *A61K 31/431* (2013.01); *A61K 31/545* (2013.01); *A61K 47/02* (2013.01); *A61K 47/12* (2013.01); *A61K 47/183* (2013.01); *A61K 31/43* (2013.01)
USPC ............................ 424/400; 514/192; 514/200

(58) Field of Classification Search
CPC ........ A61K 9/19; A61K 31/43; A61K 31/545
USPC .................. 424/400; 514/192, 200
See application file for complete search history.

(56) References Cited

U.S. PATENT DOCUMENTS

| | | |
|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,418,058 A | 11/1983 | Hirai et al. |
| 4,420,477 A | 12/1983 | Takaya et al. |
| 4,423,213 A | 12/1983 | Takaya et al. |

(Continued)

FOREIGN PATENT DOCUMENTS

| | | |
|---|---|---|
| AU | 614793 B1 | 5/1989 |
| AU | 707730 B2 | 5/1996 |

(Continued)

OTHER PUBLICATIONS

Miller et al., "Pharmacokinetics and Safety of Intravenous Ceftolozane-Tazobactam in Healthy Adult Subjects following Single and Multiple Ascending Doses", Antimicrobial Agents and Chemotherapy, vol. 56, No. 6, pp. 3086-3091 (2012).*

(Continued)

*Primary Examiner* — Kevin E Weddington

(74) *Attorney, Agent, or Firm* — Lathrop & Gage LLP; Brian C. Trinque

(57) ABSTRACT

Pharmaceutical compositions can include ceftolozane lyophilized in the absence of tazobactam.

30 Claims, 13 Drawing Sheets

(56) References Cited

U.S. PATENT DOCUMENTS

| | | |
|---|---|---|
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,529,592 A | 7/1985 | Micetich et al. |
| 4,546,101 A | 10/1985 | Takaya et al. |
| 4,550,102 A | 10/1985 | Teraji et al. |
| 4,559,334 A | 12/1985 | Takaya et al. |
| 4,562,073 A | 12/1985 | Micetich et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,616,083 A | 10/1986 | Shima et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,769,183 A | 9/1988 | Kawamata et al. |
| 4,808,617 A | 2/1989 | Kaplan et al. |
| 4,808,711 A | 2/1989 | Shimizu et al. |
| 4,822,785 A | 4/1989 | Ishibashi et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,925,934 A | 5/1990 | Taniguchi et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,194,432 A | 3/1993 | Takaya et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,207,661 B1 | 3/2001 | Thompson et al. |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,660,855 B2 | 12/2003 | Shimabayashi et al. |
| 6,774,104 B1 | 8/2004 | Sawai et al. |
| 6,800,621 B2 | 10/2004 | Nishitani et al. |
| 6,878,686 B2 | 4/2005 | Marquess et al. |
| 6,936,711 B2 | 8/2005 | Deshpande et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,112,565 B2 | 9/2006 | Sawai et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,273,935 B2 | 9/2007 | Deshpande et al. |
| 7,279,458 B2 | 10/2007 | Fatheree et al. |
| 7,304,075 B2 | 12/2007 | Araki et al. |
| 7,332,471 B2 | 2/2008 | Fatheree et al. |
| 7,341,993 B2 | 3/2008 | Fatheree et al. |
| 7,384,928 B2 | 6/2008 | Nishitani et al. |
| 7,417,143 B2 | 8/2008 | Gnanaprakasam et al. |
| 7,547,777 B2 | 6/2009 | Tokumaru et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,674,898 B2 | 3/2010 | Shimabayashi et al. |
| 7,728,127 B2 | 6/2010 | Fatheree et al. |
| 7,842,683 B2 | 11/2010 | Koppel |
| 7,915,229 B2 | 3/2011 | Cohen et al. |
| 8,133,883 B2 | 3/2012 | Cohen et al. |

(56) References Cited

U.S. PATENT DOCUMENTS

| | | |
|---|---|---|
| 8,476,425 B1 | 7/2013 | Lai et al. |
| 2002/0115650 A1 | 8/2002 | Glinka |
| 2002/0193587 A1 | 12/2002 | Shimabayashi et al. |
| 2003/0130173 A1 | 7/2003 | Fatheree et al. |
| 2003/0232983 A1 | 12/2003 | Deshpande et al. |
| 2004/0248875 A1 | 12/2004 | Ohki et al. |
| 2005/0004094 A1 | 1/2005 | Yamanaka et al. |
| 2005/0096306 A1 | 5/2005 | Yamanaka et al. |
| 2005/0171077 A1 | 8/2005 | Ruppen et al. |
| 2005/0228176 A1 | 10/2005 | Gnanaprakasam et al. |
| 2006/0051412 A1 | 3/2006 | Petereit et al. |
| 2006/0084639 A1 | 4/2006 | Cohen et al. |
| 2006/0099253 A1 | 5/2006 | Becker et al. |
| 2006/0173177 A1 | 8/2006 | Gego et al. |
| 2006/0241017 A1 | 10/2006 | Chandran |
| 2006/0269485 A1 | 11/2006 | Friedman et al. |
| 2006/0287244 A1 | 12/2006 | Chandran |
| 2006/0293516 A1 | 12/2006 | Wada et al. |
| 2007/0054899 A1 | 3/2007 | Park et al. |
| 2007/0116770 A1 | 5/2007 | Garms et al. |
| 2007/0219191 A1 | 9/2007 | Nishitani et al. |
| 2007/0286817 A1 | 12/2007 | Tatapudy et al. |
| 2007/0286818 A1 | 12/2007 | Tatapudy et al. |
| 2008/0015156 A1 | 1/2008 | Udayampalayam Palanisamy et al. |
| 2008/0160067 A1 | 7/2008 | Boeckh et al. |
| 2008/0233196 A1 | 9/2008 | Cattaneo et al. |
| 2009/0098088 A1 | 4/2009 | Taylor et al. |
| 2009/0137460 A1 | 5/2009 | Marquess et al. |
| 2009/0155387 A1 | 6/2009 | Zhang |
| 2009/0156517 A1 | 6/2009 | Zhang |
| 2009/0156518 A1 | 6/2009 | Zhang |
| 2009/0186865 A1 | 7/2009 | Diago et al. |
| 2009/0227554 A1 | 9/2009 | Liversidge et al. |
| 2009/0274662 A1 | 11/2009 | Magowan et al. |
| 2009/0275552 A1 | 11/2009 | Patel et al. |
| 2009/0291102 A1 | 11/2009 | Fortin |
| 2009/0311234 A1 | 12/2009 | Koski et al. |
| 2010/0040548 A1 | 2/2010 | Yu |
| 2010/0286031 A1 | 11/2010 | Charan et al. |
| 2011/0044917 A1 | 2/2011 | Tosetti |
| 2011/0136763 A1 | 6/2011 | Xia et al. |
| 2011/0190252 A1 | 8/2011 | Watson et al. |
| 2011/0257079 A1 | 10/2011 | Chaudhary et al. |
| 2013/0065874 A1 | 3/2013 | Chandorkar et al. |
| 2014/0187528 A1 | 7/2014 | Lai et al. |
| 2014/0206659 A1 | 7/2014 | Lai et al. |
| 2014/0213567 A1 | 7/2014 | Lai et al. |
| 2014/0262868 A1 | 9/2014 | Terracciano et al. |
| 2014/0274989 A1 | 9/2014 | Terracciano et al. |
| 2014/0274990 A1 | 9/2014 | Terracciano et al. |
| 2014/0274991 A1 | 9/2014 | Damour et al. |
| 2014/0274992 A1 | 9/2014 | Damour et al. |
| 2014/0274993 A1 | 9/2014 | Terracciano et al. |
| 2014/0274994 A1 | 9/2014 | Damour et al. |
| 2014/0274995 A1 | 9/2014 | Zhou et al. |
| 2014/0274996 A1 | 9/2014 | Damour et al. |
| 2014/0274997 A1 | 9/2014 | Zhou et al. |
| 2014/0274998 A1 | 9/2014 | Terracciano et al. |
| 2014/0275000 A1 | 9/2014 | Damour et al. |
| 2014/0303136 A1 | 10/2014 | Terracciano et al. |
| 2014/0309205 A1 | 10/2014 | Terracciano et al. |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 A1 | 4/1988 |
| CA | 2140701 A1 | 7/1995 |
| CN | 99100092 | 12/1999 |
| CN | 200410067367 | 4/2006 |
| CN | 200810092568 | 10/2008 |
| CN | 200810238479 | 5/2009 |
| CN | 200910169647 | 4/2010 |
| CN | 201010557481 | 4/2011 |
| CN | 201110061045 | 3/2012 |
| EP | 0047977 A1 | 9/1981 |
| EP | 0097446 A1 | 1/1984 |
| EP | 0137440 | 4/1985 |
| EP | 0137442 A2 | 4/1985 |
| EP | 0138552 | 4/1985 |
| EP | 0111934 B1 | 8/1988 |
| EP | 0318767 A2 | 6/1989 |
| EP | 0664117 A1 | 7/1995 |
| EP | 0711774 B1 | 5/1996 |
| EP | 0771803 A1 | 5/1997 |
| EP | 1273586 A1 | 1/2003 |
| EP | 1285923 A1 | 2/2003 |
| EP | 1468697 A1 | 10/2004 |
| EP | 1134222 B1 | 4/2005 |
| EP | 1554287 | 7/2005 |
| EP | 1671974 A1 | 6/2006 |
| EP | 1686131 A2 | 8/2006 |
| EP | 1759697 A1 | 3/2007 |
| EP | 1787641 A1 | 5/2007 |
| EP | 1959933 | 8/2008 |
| EP | 1974721 A1 | 10/2008 |
| EP | 2015755 | 1/2009 |
| EP | 2062581 A1 | 5/2009 |
| EP | 2062582 A1 | 5/2009 |
| EP | 2062585 A1 | 5/2009 |
| EP | 2136844 | 12/2009 |
| EP | 2305251 A2 | 4/2011 |
| EP | 1154770 | 11/2011 |
| JP | 62103092 A | 5/1987 |
| JP | 62158290 A | 7/1987 |
| JP | 63051388 A | 3/1988 |
| JP | 63051389 A | 3/1988 |
| JP | 2088582 A | 3/1990 |
| JP | 2117678 A | 5/1990 |
| JP | 4288086A A | 10/1992 |
| JP | 5222058 A | 8/1993 |
| JP | 6056848 A | 3/1994 |
| JP | 6128268 A | 5/1994 |
| JP | 2005162670 A | 6/2005 |
| WO | 9512601 A1 | 5/1995 |
| WO | 9741128 A1 | 11/1997 |
| WO | WO 99/28308 | 6/1999 |
| WO | WO 99/64049 | 12/1999 |
| WO | WO0004915 A1 | 2/2000 |
| WO | 0050035 A2 | 8/2000 |
| WO | 02090363 A1 | 11/2002 |
| WO | 02090364 A1 | 11/2002 |
| WO | 02092605 A1 | 11/2002 |
| WO | 02102378 A1 | 12/2002 |
| WO | 03066053 A1 | 8/2003 |
| WO | WO 03/078440 | 9/2003 |
| WO | 03104241 A1 | 12/2003 |
| WO | 2004019901 A1 | 3/2004 |
| WO | 2004039776 A2 | 5/2004 |
| WO | WO 2004/048551 | 6/2004 |
| WO | 2004066976 A1 | 8/2004 |
| WO | 2004098643 A1 | 11/2004 |
| WO | WO 2005/005436 | 1/2005 |
| WO | 2005074925 A1 | 8/2005 |
| WO | 2006044600 A1 | 4/2006 |
| WO | 2006045006 A1 | 4/2006 |
| WO | 2006088305 A1 | 8/2006 |
| WO | 2007065862 A1 | 6/2007 |
| WO | 2007086011 A1 | 8/2007 |
| WO | 2007086013 A1 | 8/2007 |
| WO | 2007086014 A1 | 8/2007 |
| WO | 2007099396 A2 | 9/2007 |
| WO | 2007129176 A2 | 11/2007 |
| WO | 2007145866 A1 | 12/2007 |
| WO | 2007145868 A1 | 12/2007 |
| WO | 2008030469 A2 | 3/2008 |
| WO | 2008065247 A1 | 6/2008 |
| WO | 2008075207 A2 | 6/2008 |
| WO | 2008101743 A2 | 8/2008 |
| WO | 2008113177 A1 | 9/2008 |
| WO | 2009048603 A1 | 4/2009 |

(56) References Cited

FOREIGN PATENT DOCUMENTS

| WO | WO 2009/105782 | 8/2009 |
|---|---|---|
| WO | 2009122252 A2 | 10/2009 |
| WO | 2009134948 A1 | 11/2009 |
| WO | 2010014285 A1 | 2/2010 |
| WO | 2010142241 A1 | 12/2010 |
| WO | 2011101710 A1 | 8/2011 |
| WO | 2011112435 A1 | 9/2011 |
| WO | 2011127200 A2 | 10/2011 |
| WO | WO2013036783 A2 | 3/2013 |
| WO | WO 2014/052799 | 4/2014 |

OTHER PUBLICATIONS

Bulik et al, In vivo comparison of CXA-101 with and without tazobactam versus piperacillin-tazobactam using human simulated exposures against phenotypically diverse gram-negative organisms. Antimicrob Agent Chemother 2012 56 (1):544-9.
Bulik et al., In vitro potency of CXA-101, a novel cephalosporin, against *Pseudomonas aeruginosa* displaying various resistance phenotypes, including multidrug resistance. Antimicrob Agents Chemother. 2010;54(1):557-9.
Chandorkar et al., Intrapulmonary penetration of ceftolozane/tazobactam and piperacillin/tazobactam in healthy adult subjects. J Antimicrob Chemother. 2012, 67, 2463.
Clinical and Laboratory Standards Institute CLSI Document M07-A9.
Clinical and Laboratory Standards Institute CLSI Document M100-S22.
Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 , 54: 3427-31.
Juan et al., Activity of a new antipseudomonal cephalosporin, CXA-101, against carbapenem-resistant and multidrug-resistant *Pseudomonas aeruginosa* clinical strains. Antimicrob Agents Chemother. 2010;54(2):846-51.
Livermore et al., Chequerboard titration of cephalosporin CXA-101 and tazobactam versus beta-lactamase-producing Enterobacteriaceae. J Antimicrob Chemother. 2010 65 1972-4.
Miller et al., Pharmacokinetics and Safety of Intravenous Ceftolozane/tazobactam in Healthy Adult Subjects following Single and Multiple Ascending Doses. Antimicrob Agents Chemother. 2012 56:3086-91.
Moya et al., Activity of a new cephalosporin, CXA-101 (FR264205), against beta-lactam-resistant *Pseudomonas aeruginosa* mutants selected in vitro and after antipseudomonal treatment of intensive care unit patients. Antimicrob Agents Chemother. 2010 ;54(3):1213-7.
Moya et al., Affinity of the New Cephalosporin CXA-101 to Penicillin-Binding Proteins of *Pseudomonas aeruginosa*. Antimicrob Agents Chemother. 2010; 54: 3933-3937.
Moya et al., Pan-Beta-Lactam Resistance Development in *Pseudomonas aeruginosa* Clinical Strains: Molecular Mechanisms, Penicillin-Binding Protein Profiles, and Binding Affinities. Antimicrob Agents Chemother. 2012 56 4771-8.
Perletti et al., CXA-101—Cephalosporin Antibiotic. Drugs of the Future 2010; 35(12): 977-986.
Riera et al., Anti-biofilm and resistance suppression activities of CXA-101 against chronic respiratory infection phenotypes of *Pseudomonas aeruginosa* strain PAO1. J Antimicrob Chemother. 2010;65(7):1399-1404.
Sader et al., Antimicrobial activity of CXA-101, a novel cephalosporin tested in combination with tazobactam against Enterobacteriaceae, *Pseudomonas aeruginosa*, and *Bacteroides fragilis* strains having various resistance phenotypes. Agents Chemother. 2011 55(5):2390-4.
Zamorano et al., Activity of the new cephalosporin CXA-101 against *Pseudomonas aeruginosa* isolates from chronically-infected cystic fibrosis patients. Clin Microbiol Infect. 2010 16(9):1482-7.

Alexov et al. Efficacy of Ampicillin-Sulbactam Is not Dependent upon Maintenance of a Critical Ratio between Components: Sulbactam Pharmacokinetics in Pharmacodynamic Interactions. Antimcirobial Agents Chemotherapy 1996;40:2468.
Bush et al. Kinetic Interactions of Tazobactam with Beta-Lactamases from All Major Structural Classes. Antimicrobial Agents and Chemotherapy 1993;37:851.
Hatano et al. In vivo Anti-*Pseudomonas aeruginosa* Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.
Kurpiel. Point Mutations in the Inc Antisense RNA Gene Are Associated with Increased Plasmid Copy Number, Expression of BIaCMY-2 and Resistance to Piperacillin/Tazobactam in *Escherichia coli*. Journal of Antimicrobial Chemotherapy 2012;67:339.
Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.
Louie et al., Pharmacodynamics of b-Lactamase Inhibition by NXL104 in Combination with Cefaroline: Examining Organisms with Multiple Types of b-Lacramases. Antimicrobial Agents and Chemotherapy. 2012, 56, 258.
Miller et al. CXA-201 dose selection based on probability of target attainment and drug exposure in subjects with varying degrees of renal impairment. ICAAC 2011. Oral Presentation A-1099.
Seetulsingh et al. Activity of Clavulanate Combinations against TEM-1 b-Lactamase-Producing *Escherichia coli* Isolates Obtained in 1982 and 1989. Journal of Antimicrobial Chemotherapy 1991;27:749.
Soon et al. A Novel Mathematical Modeling Approach to Characterize the Pharmacodynamics of Ceftolozane/ Tazobactam, a β-lactam & β-lactannase Inhibitor Combination. 52nd Annual Interscience Conference on Antimicrobial and Chemotherapy (ICAAC 2012); Sep. 9-12, 2012. Oral Presentation A-1762.
Steenbergen et al. Potency of CXA-101Tazobactam for Pathogens from ICU and non-ICU Correlated to Probability of Pharmacokinetic/Pharmacodynamic (PK/PD) Target Attainment. ICAAC 2011. Oral Presentation A-1689.
Strayer et al. Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.
Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.
European Committee on Antimicrobial Sus Testing 2012.
Giske et al, 'Activity of Cephalosporin CXA-101 and Comparators against Extended-spectrum-beta-lactamase—producing *Pseudomonas aeruginosa*'. Journal of Antimicrobial Chemotherapy 2009, vol. 64, No. 2, pp. 430-431.
Jacqueline et al, 'Efficacy of Ceftolozane in a Murine Model of *Pseudomonas aeruginosa* acute pneumonia: in vivo Antimicrobial Activity and Impact on Host Inflammatory Response'. Journal of Antimicrobial Chemotherapy 2012, vol. 68, No. 1, pp. 1-7.
Livermore et al, 'Activity of Cephalosporin CXA-101 against *Pseudomonas aeruginosa* and *Burkholderia cepacia* strains and Isolates'. International Journal of Antimicrobial Agents 2009, vol. 34, No. 5, pp. 402-406.
Takeda et al, 'Stability of FR264205 against AmpC beta-lactamase of *Pseudomonas aeruginoas*'. International Journal Antimicrobial Agents, 2007. vol. 30, No. 5, pp. 443-445.
Takeda et al., In vitro and in vivo activities of a new cephalosporin, FR264205, against *Pseudomonas aeruginosa*. Antimicrob Agents Chemother. 2007; 51(3):826-30.
Titelman et al, 'In vitro Activity of CXA-101 Plus Tazobactum against CTX-M-14 and CTX-M-15-producing *Escherichia* and *Klebsiella pneumoniae*'. Diagnostic Microbiology and Infectious Disease. 2011, vol. 70, No. 1, pp. 137-141.

(56) References Cited

OTHER PUBLICATIONS

Toda et al, Synthesis and SAR of Novel Parenteral Anti-pseudomonal cephalosporins: Discovering of FR264205. Med Chem Lett. 2008, vol. 18, No. 17, pp. 4849-4852.

Anderegg et al: Quality Control Guidelines for BAL9141 (Ro 63-9141), an Investigational Cephalosporin, When Reference MIC and Standardized Disk Diffusion Susceptibility Test Methods Are Used; Journal of Clinical Microbiology. (2004), pp. 3356-3358.

Farrell: Antimicrobial Activity of Ceftolozane-Tazobactam Tested against Enterobacteriaceae with Various Resistance Patterns Isolated in U.S. Hospitals; Antimicrobial Agents and Chemotherapy; (2013) vol. 57 No. 12 pp. 6305-6310.

International Preliminary Report on Patentability for for PCT/US2012/054191, dated Mar. 12, 2014, 8 pages.

International Search Report for PCT/US2012/054191, dated Feb. 20, 2013, 4 pages.

Marunaka: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H), in Aqueous Solutions and Alkaline MEthanol Solution: Pathway and Structural Elucidation of Products; Chem. Pharm. Bull.; 1988, vol. 36, pp. 4478-4487.

Matsushima: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H) in Solid State: Structural Eldcidation; Chem. Pharm. Bull.; 1988, vol. 36, pp. 4593-4596.

Murano: Structural requirements for the stability of novel cephalosporins to AmpC beta-lactamase based on 3-D structure; Bioorg. Med. Chem. Lett.; 2007, vol. 16, pp. 2261-2275.

Search Request Confirmation; Science IP; Dec. 6, 2010, 3 pages.

Sutcliffe et al: Multidrug-Resistant Gram-Negative Pathogens: New Strategies; Tetraphase Pharmaceuticals . Retrieved online from: http://www.tufts.edu/med/apua/practitioners/resources_23_2817980013.pdf Retrieved Mar. 19, 2014.

U.S. National Institutes of Health, 'Safety and Efficacy Study of Ceftolozane/Tazobactam to Treat Ventilated Nosocomial Pneumonia (ASPECT-NP)'. Sponsored by Cubist Pharmaceuticals. http://www.clinicaltrials.gov/ct2/show/NCT02070757?term=ceftolozane &rank=1 Updated Feb. 21, 2014. ClinicalTrials.gov Identifier: NCT02070757 (Study not yet open for participant recruitment).

U.S. National Institutes of Health, 'Safety and Efficacy Study of IV CXA-101 and IV Ceftazidime in Patients with Complicated Urinary Tract Infections'. Sponsored by Cubist Pharmaceuticals. http://www.clinicaltrials.gov/ct2/show/ NCT00921024?term=ceftolozane& rank=4 Updated Aug. 5, 2010. ClinicalTrials.gov Identifier: NCT00921024 (Study has been completed).

U.S. National Institutes of Health, 'Safety and Efficacy Study to Compare IV CXA 101/Tazobactam and Metronidazole With Meropenem in Complicated Intraabdominal Infections'. Sponsored by Cubist Pharmaceuticals. http://www.clinicaltrials.gov/ct2/show/NCT01147640?term=ceftolozane&rank=2 Updated May 5, 2011. ClinicalTrials.gov Identifier: NCT01147640 (Study has been completed).

U.S. National Institutes of Health, 'Study of Intravenous Ceftolozane/Tazobactam vs. Piperacillin/Tazobactam in Ventilator Associated Pneumonia'. Sponsored by Cubist Pharmaceuticals. http://www.clinicaltrials.gov/ct2/show/ NCT01853982?term=ceftolozane&rank=3 Updated Jan. 28, 2014. ClinicalTrials.gov Identifier: NCT01853982 (Study has been terminated).

Wootton et al: BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.

Written Opinion of the International Searching Authority for PCT/US2012/054191, dated Feb. 20, 2013, 7 pages.

Yoshizawa: New broad-spectrun parenteral cephalosporins exhibiting potent activity against both methicilln-resistant *Staphlococcus aureus* (MRSA) and *Pseudomonas aeruginosa*. Part 3: &Beta[2-(5-Amino-1,2,4-thiadiazol-3-yl)-2- ethoxtiminoacetamido] cephalosporins bearing 4-[3-(aminoalkyl)-ureido]-1-pyridinium at C3; Bioorg. Med. Chem. Lett.; 2004, vol. 12, pp. 4221-4231.

Brown, R.F. et al. 'Synthesis and Biological Evaluation of a Series of Parental 3'-Quaternary Ammonium Cephalosporins.sup.1' Journal of Medicinal Chemistry. 1990, vol. 33, No. 8, pp. 2114-2121.

Sakagami, K. et al. 'Synthetic Cephalosporins. VI..sup.1) Synthesis and Antibacterial Activity of 7-[(Z)-2-(2-Aminothiazol-4-YL)-2-(1-Carboxy-1-Methyl)Ethoxyiminoacetamido- ]-3-(3-Hydroxy-4-Pyridon-1-YL)Methyl-3-Cephem-4-Carboxylic Acid and Related Compounds'. Chemical and Pharmaceutical Bulletin. 1990, vol. 38, No. 8, pp. 2271-2273.

English Translation of Abstract for Japanese Patent No. JP 04-288286, published Oct. 13, 1992, 3 pages.

Abstract for Sader et al. 'Antimicrobial Activity of Ceftolozane/Tazobactam Tested Against Gram-negative Bacterial Isolates from Hospitalized Patients with Pneumonia in United States (USA) and European (EU) Hospitals (2012)'. 53rd Annual Interscience Conference on Antimicrobial Agents and Chemotherapy (ICAAC 2013); Sep. 10-13, 2013; Denver, CO. Poster C2-1633.

Abstract for Sader et al. 'Post Beta-Lactamase Inhibitor Effect of Tazobactam When Associated with Ceftolozane and Tested against ESBL-Producing Strains'. 53rd Annual Interscience Conference on Antimicrobial Agents and Chemotherapy (ICAAC 2013); Sep. 10-13, 2013; Denver, CO. Poster A-1030.

Abstract for Vanscoy et al. 'Relationship between Ceftolozane/Tazobactam (TOL/TAZ) Exposure and *E. coli* Resistance Amplification Prevention in a Hollow Fiber Infection Model (HFIM)'. 53rd Annual Interscience Conference on Antimicrobial Agents and Chemotherapy (ICAAC 2013); Sep. 10-13, 2013; Denver, CO. Poster A-1031.

Abstract for Vanscoy et al. 'Identification of a Translational Relationship Between Tazobactam (TAZ) Exposure in Combination with Ceftolozane (TOL) and Efficacy Against ESBL-Producing Enterobacteriaceae'. 53rd Annual Interscience Conference on Antimicrobial Agents and Chemotherapy (ICAAC 2013); Sep. 10-13, 2013; Denver, CO. Poster A-1032.

Abstract for Zhanel et al. 'In Vitro Activity of Ceftolozane/Tazobactam Against 5,715 Gram-Negative and Gram-Positive Pathogens Isolated from Patients in Canadian Hospitals in 2011 and 2012: Canward Surveillance Study'. 53rd Annual Interscience Conference on Antimicrobial Agents and Chemotherapy (ICAAC 2013); Sep. 10-13, 2013; Denver, CO. Poster E-1689.

Abstract for Zilberberg et al. 'Multidrug resistant *Pseudomonas aeruginosa* among hospitalized patients with pneumonia, US 2000-2009'. Making a Difference in Infectious Diseases Pharmacotherapy Conference (MAD-ID 2013); May 9-11, 2013; Orlando, FL. Encore Presentation from ISICEM 2013.

Abstract for Zilberberg et al. 'Gram-negative resistance and need for ICU among urinary tract infections in the US'. Making a Difference in Infectious Diseases Pharmacotherapy Conference (MAD-ID 2013); May 9-11, 2013; Orlando, FL. Encore Presentation from ISICEM 2013.

Abstract for Zilberberg et al. 'Multidrug resistance among *P. aeruginosa* and Enterobacteriaceae in the US hospitals, 2000-2009'. Making a Difference in Infectious Diseases Pharmacotherapy Conference (MAD-ID 2013); May 9-11, 2013; Orlando, FL. Encore Presentation from SCCM 2013.

Abstract for Chandorkar et al. 'Target Attainment Rates (TAR) and Cumulative Fraction of Response (CFR) in Plasma for Ceftolozane in a Simulated Population of Patients with Complicated Intra-abdominal (cIAI) and Urinary Tract Infection (cUTI)'. 23rd Annual Meeting of the European Congress of Clinical Microbiology (ECCMID 2013); Apr. 27-30, 2013; Berlin, Germany. Poster P2742.

Abstract for Halimi et al. 'Comparative Evaluation of Ceftolozane/tazobactam MIC testing with Etest® and CLSI Broth Microdilution Methods'. 23rd Annual Meeting of the European Congress of Clinical Microbiology (ECCMID 2013); Apr. 27-30, 2013; Berlin, Germany. Poster P1606.

Abstract for Reynolds et al. '*Pseudomonas aeruginosa* in the UK and Ireland: Susceptibility to Old and New Agents'. 23rd Annual Meeting of the European Congress of Clinical Microbiology (ECCMID 2013); Apr. 27-30, 2013; Berlin, Germany. Poster P1519.

(56) References Cited

OTHER PUBLICATIONS

Abstract for Sader et al. 'Antimicrobial activity of ceftolozane/tazobactam and comparator agents tested against *Pseudomonas aeruginosa* strains from 14 European countries and Israel'. 23rd Annual Meeting of the European Congress of Clinical Microbiology (ECCMID 2013); Apr. 27-30, 2013; Berlin, Germany. Poster P337.

Abstract for Noel et al. 'Pharmacodynamics of Ceftolozane/Tazobactam Against Gram Negative Bacilli'. 53rd Annual Interscience Conference on Antimicrobial Agents and Chemotherapy (ICAAC 2013); Sep. 10-13, 2013; Denver, CO. Poster.

Abstract for Melchers et al. 'Pharmacokinetics of Tazobactam and Ceftolozane Alone and in Combination in Mice'. 53rd Annual Interscience Conference on Antimicrobial Agents and Chemotherapy (ICAAC 2013); Sep. 10-13, 2013; Denver, CO. Poster A-1033.

Abstract for Melchers et al. 'Pharmacodynamics of Ceftolozane Combined with Tazobactam in a Neutropenic Mouse Thigh Model'. 53rd Annual Interscience Conference on Antimicrobial Agents and Chemotherapy (ICAAC 2013); Sep. 10-13, 2013; Denver, CO. Poster A-1034.

Abstract for Lucasti et al. 'A Multicenter, Double-Blind, Randomized, Phase 2 Study to Assess the Safety and Efficacy of Ceftolozane/Tazobactam (TOL/TAZ) plus Metronidazole (MTZ) Compared to Meropenem (MER) in Adult Patients with Complicated Intra-abdominal Infections (cIAI)'. 53rd Annual Interscience Conference on Antimicrobial Agents and Chemotherapy (ICAAC 2013); Sep. 10-13, 2013; Denver, CO. Poster K-1709.

Abstract for Estabrook et al. 'In vitro Activity of CXA-201 (Ceftolozane-Tazobactam) Against 200 CTX M-Producing *Escherichia coli* Clinical Isolates'. 53rd Annual Interscience Conference on Antimicrobial Agents and Chemotherapy (ICAAC 2013); Sep. 10-13, 2013; Denver, CO. Poster E-1169.

Abstract for Bulik et al. 'In vitro activity of CXA-101, a novel cephalosporin, against resistant phenotypes of *Pseudomonas aeruginosa*'. 47th Annual Meeting of the Infectious Diseases Society (IDSA 2009); Oct. 29-Nov. 1, 2009; Philadelphia, PA. Poster 209.

Abstract for Moya et al. 'Activity of CXA-101 against *Pseudomonas aeruginosa* beta-lactam resistance mechanisms: ampD, ampDh2, ampDh2, dacB, and oprD mutations'. 49th Annual Interscience Conference on Antimicrobial Agents and Chemotherapy (ICAAC 2009); Sep. 12-15, 2009; San Francisco, CA. Poster F1-1989.

Abstract for Livermore et al. 'Chequerboard titrations of cephalosporin CXA-101 and tazobactam vs. beta-lactamase producing Enterobacteriaceae'. 49th Annual Interscience Conference on Antimicrobial Agents and Chemotherapy (ICAAC 2009); Sep. 12-15, 2009; San Francisco, CA. Poster F1-1994.

Abstract for Jacqueline et al. 'ED50 Determination of CXA-101 Alone and in Combination with Tazobactam for Treating Experimental Peritonitis in Mice Due to ESBL-Producing *Klebsiella pneumoniae* strains: Comparison with Ceftazidime and Piperacillin/Tazobactam'. 50th Annual Interscience Conference on Antimicrobial Agents and Chemotherapy (ICAAC 2010); Sep. 12-15, 2010; Boston, MA. Poster B-708.

Abstract for Cabot et al. '*Pseudomonas aeruginosa* Ceftolozane/Tazobactam Resistance Development Requires Multiple Mutations Leading to Overexpression and Structural Modification of AmpC'. 53rd Annual Interscience Conference on Antimicrobial Agents and Chemotherapy (ICAAC 2013); Sep. 10-13, 2013; Denver, CO. Poster C1-060.

Abstract for Jacqueline. 'In vivo Activity of CXA-101 against *Pseudomonas aeruginosa* in a Rabbit Experimental Pneumonia: Comparison with Ceftazidime Piperacillin-Tazobactam and Imipenem'. 51st Annual Interscience Conference on Antimicrobial Agents and Chemotherapy (ICAAC 2011); Sep. 17-20, 2011; Chicago, IL. Poster B-590.

Abstract for Reynolds et al. 'Enterobacteriaceae in the UK and Ireland: Susceptibility to Old and New Agents'. 52nd Annual Interscience Conference on Antimicrobial Agents and Chemotherapy (ICAAC 2012); Sep. 9 12, 2012; San Francisco, CA. Poster C2-152.

Abstract for Miller et al. 'Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population'. 52nd Annual Interscience Conference on Antimicrobial Agents and Chemotherapy (ICAAC 2012); Sep. 9-12, 2012; San Francisco, CA. Poster A-624.

Abstract for Melchers et al. 'In vitro Activity of CXA-101 Alone and in Combination With Tazobactam Against Extended Spectrum Beta-lactamase Harbouring Enterobacteriaceae'. 52nd Annual Interscience Conference on Antimicrobial Agents and Chemotherapy (ICAAC 2012); Sep. 9-12, 2012; San Francisco, CA. Poster E 198.

Abstract for Zilberberg et al. 'Prevalence of beta-lactam resistance among *P. aeruginosa* in US hospitals, 2000-2009'. To be presented at the 2nd Annual IDWeek (IDWeek 2013); Oct. 2-6, 2013; San Francisco, CA. Poster #1580.

Abstract for Cabot et al. 'Dynamics and mechanisms of resistance development to ceftazidime, meropenem and ceftolozane-/tazobactam in wild-type and mutator *P. aeruginosa* strains'. 52nd Annual Interscience Conference on Antimicrobial Agents and Chemotherapy (ICAAC 2012); Sep. 9-12, 2012; San Francisco, CA. Poster C1-1970.

Abstract for Sader et al. 'Frequency of occurrence and antimicrobial susceptibility of Gram-negative organisms isolated from health care associated urinary tract infections: Results from the Program to Assess Ceftolozane/Tazobactam Susceptibility (PACTS)'. To be presented at the 2nd Annual IDWeek (IDWeek 2013); Oct. 2-6, 2013; San Francisco, CA. Poster.

Abstract for Zilberberg et al. 'Secular trends in gram-negative resistance among urinary tract infection hospitalizations in the US, 2000-2009'. 23rd Annual Meeting of the European Congress of Clinical Microbiology (ECCMID 2013); Apr. 27-30, 2013; Berlin, Germany. Poster P1517.

Abstract for Vanscoy et al. 'Pharmacokinetics-Pharmacodynamics (PK-PD) of Tazobactam in Combination with Ceftolozane in an In Vitro Infection Model'. 23rd Annual Meeting of the European Congress of Clinical Microbiology (ECCMID 2013); Apr. 27-30, 2013; Berlin, Germany. Poster P900.

Abstract for Sader et al. 'Ceftolozane/tazobactam activity tested against aerobic Gram-negative organisms isolated from intraabdominal infections in European and United States hospitals (2012)'. To be presented at the 2nd Annual IDWeek (IDWeek 2013); Oct. 2-6, 2013; San Francisco, CA. Poster #698.

Abstract for Sader et al. 'Antimicrobial susceptibility of gram-negative bacteria causing urinary tract infections in European and United States hospitals (2009-2011)'. 23rd Annual Meeting of the European Congress of Clinical Microbiology (ECCMID 2013); Apr. 27-30, 2013; Berlin, Germany. Poster P1516.

Abstract for Chandorkar et al. 'Population Pharmacokinetics (PPK) Meta-Analysis of Ceftolozane/Tazobactam in Healthy Volunteers and Patients'. Presented at the Annual Meeting of the American College of Clinical Pharmacy (ACCP 2013); Oct. 13-16, 2013; Albuquerque, NM. Poster # 120.

Abstract for Chandorkar et al. 'Pharmacokinetics and Safety of Ceftolozane/Tazobactam in Subjects with Severe Renal Impairment or End Stage Renal Disease on Hemodialysis'. To be presented at the 2nd Annual IDWeek (IDWeek 2013); Oct. 2-6, 2013; San Francisco, CA. Poster #723.

Abstract for Sader et al. 'Antimicrobial activity of ceftolozane/tazobactam and comparator agents tested against *Pseudomonas aeruginosa* isolates from United States (USA) medical centers (2011-2012)'. To be presented at the 2nd Annual IDWeek (IDWeek 2013); Oct. 2-6, 2013; San Francisco, CA. Poster #695.

Abstract for Brown et al. Activity profile of CXA-101 against gram-positive and gram-negative pathogens by broth and agar dilution. 48th Annual Interscience Conference on Antimicrobial Agents and Chemotherapy & the infectious Disease Society of America 46th Annual Meeting (ICAAC/IDSA 2008); Oct. 25-28, 2008. Poster F1-354; This poster is obtainable at: http://www.eurofins.com/media/694466/Calixe/020F1-354%20broth%20agar%20v6.pdf.

Abstract for Brown et al. Activity profile of CXA-101 and CXA-101/tazobactam against target gram-positive and gram-negative pathogens. 49th Annual Interscience Conference on Antimicrobial Agents

(56) References Cited

OTHER PUBLICATIONS and Chemotherapy (ICAAC 2009); 12th-15th, 2009. Poster F1-1986; This poster is obtainable at http://www.eurofins.com/media/767069/Final%20F1-1986.pdf.

Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http://www.eurofins.com/media/694469/CW/020F1-357%20parameter%20v6.pdf.

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358°/020tV/020mbe/020v5.pdf.

Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); 12th-15th, 2009. Poster F1-1998; This poster is obtainable at: http:/lwww.eurofins.com/media/767072/Final%20F1-1998.pdf.

Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Bulik et al. In vivo Comparison of CXA-101 (FR264205) with and without Tazobactam verus Piperacillin-Tazobactam Using Human Simulated Exposures against Phenotypically Diverse Gram-Negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of *P. aeruginosa* Blood Stream Isolates Overexpressing AmpC and the Major Efflux Pumps. 50th Annual Interscience Conference on Antimicrobial Agents and Chemotherapy (ICAAC 2010); Sep. 12-15, 2010. Poster E-816.

Abstract for Chandorkar et al. Penetration of Ceftolozane/Tazobactam and Piperacillin/Tazobactam into the Epithelial lining of Fluid of Healthy Volunteers. 22nd Annual Meeting of the European Congress of Clinical Microbiology (ECCMID 2012); Mar. 31-Apr. 3, 2012. Poster P1627.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Craig et al., In vivo activity of CXA-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against *Pseudomonas aeruginosa* and other Enterobacteriaceae in the thighs of neutropenic mice. 49th Annual Interscience Conference on Antimicrobial Agents and Chemotherapy (ICAAC 2009); Sep. 12-15, 2009. Poster F1-2002.

Abstract for Fenneteau et al. Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/default/files/webform/posters/ACOP2011%20-%020Dosing%20Strategies%20of%20CXA-101%020and%20Taz%20in%20cUTI%020Patients.pdf.

Abstract for Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK and safety of CXA-101, a new antipseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.

Abstract for Ge et al., PK study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001.

Abstract for Giske et al., CXA-101 has high activity against clinical isolates of *Pseudomonas aeruginosa* including ceftazidime-resistant isolates. 49th Annual Interscience Conference on Antimicrobial Agents and Chemotherapy (ICAAC 2009); Sep. 12-15, 2009. Poster F1-1988.

Abstract for Hershberger et al. CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.

Abstract for Jacqueline . Assessment of the In vivo Activity of CXA-101 in a Murine Model of *Pseudomonas aeruginosa* Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401.

Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000.

Abstract for Jacqueline et al. FIC Index determination of CXA-101/tazobactam in combination with amikacin, aztreonam, meropenem, levofloxacin, and tigecycline against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1995.

Abstract for Jacqueline et al. In vitro assessment using time-kill curves of CXA-101/tazobactam against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1996.

Abstract for Juan et al., Oliver A. Activity of the new cephalosporin CXA-101 against carbapenem-resistant *Pseudomonas aeruginosa* isolates from a Spanish multicenter study. 49th Annual Interscience Conference on Antimicrobial Agents and Chemotherapy (ICAAC 2009); Sep. 12-15, 2009. Poster F1-1987.

Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.

Abstract for Livermore et al., Warner M. Activity of cephalosporin CXA-101 vs. *P. aeruginosa*. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webc/HPAwebFile/HPAweb_C/1225354148015.

Abstract for Marier et al. Pharmacokinetics of a novel antipseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.

(56) References Cited

OTHER PUBLICATIONS

Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.

Abstract for Hershberger et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.

Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster B1-589.

Abstract for Miller et al., Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641.

Abstract for Moulds et al., Impact of characterized resistance mechanisms on the susceptibility of *Pseudomonas aeruginosa* to CXA-101. 50th Annual Interscience Conference on Antimicrobial Agents and Chemotherapy (ICAAC Sep. 12-15, 2010. Poster C1-1415; This poster is obtainable at: http://www.cubist.com/downloads/Moulds.PP.ICAAC_2010.Impact_of_resis_mech_on_suscep_of_P_aeruginosa_to_CXA_JNS.pdf.

Abstract for Moya et al. Affinity of the new cephalosporin CXA-101 to penicillin-binding proteins of *Pseudomonas aeruginosa*. 49th Annual Interscience Conference on Antimicrobial Agents and Chemotherapy (ICAAC 2009); Sep. 12-15, 2009. Poster F1-1985.

Abstract for Moya et al. Pan-Beta-lactam resistance development in *P. aeruginosa* clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.

Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.

Abstract for Riera et al. Activity of the new cephalosporin CXA-101 against biofilms of relevant *P. aeruginosa* phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.

Abstract for Sader et al., Activity of the Novel Antimicrobial Ceftolozane)Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/IDWeek2012/846. Pdf.

Abstract for Sader et al., Activity of the Novel Antimicrobial Ceftolozane/Trazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199.

Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.

Abstract for Sader et al., Activity of the novel cephalosporin CXA-101 tested in combination with tazobactam against cephalosporin-resistant Enterobacteriaceae, *P. aeruginosa* and *B. fragilis*. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC20091F1-1992.pdf.

Abstract for Snydman et al., Activity of Ceftolozane/Tazobactam CXA-201 against 270 recent isolates from the bacteroides group. 22nd Annual Meeting of the European Congress of Clinical Microbiology (ECCMID 2012); Mar. 31-Apr. 3, 2012. Poster; This poster is obtainable at: http://www.escmid_orgtescmid_library/online_lecture_library/?search=l&current_page=l&search_term=snydman.

Abstract for Soon et al., In vitro Pharmacodynamics of CXA-201 (Ceftolozane/Tazobactam) against Beta-lactamase Producing *Eschericia coli*. 52nd Annual Interscience Conference on Antimicrobial Agents and Chemotherapy (ICAAC 2012); Sep. 9-12, 2012. Poster E-201.

Abstract for Titelman et al. Activity of CXA-101 plus tazobactam against ESBL-producing *E. coli* and *K. pneumoniae*. 49th Annual Interscience Conference on Antimicrobial Agents and Chemotherapy (ICAAC 2009); Sep. 12-15, 2009. Poster F1-1993.

Abstract for Umeh et al., A double-blind, randomized, phase 2 study to compare the safety and efficacy of intravenous CXA-101 and intravenous ceftazidime in complicated urinary tract infection. 50th Annual Interscience Conference on Agents and Chemotherapy (ICAAC 2010); Sep. 12-15, 2010. Poster L1-361A; This poster is obtainable at: http://www.cubist.com/downloads/Umeh_ICAAC2010_08144v2.pdf.

Abstract for Walkty et al. In Vitro Activity of Ceftolozane/Tazobactam (CXA-201) versus *Pseudomonas aeruginosa* Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at:https://idsa.confex.com/idsa/2012/webprogram/Handouttid509/POSTER202_1616.pdf.

Abstract for Zamorano et al. Activity of the new cephalosporin CXA-101 against *P. aeruginosa* isolates from chronically infected cystic fibrosis patients. 49th Annual Interscience Conference on Antimicrobial Agents and Chemotherapy (ICAAC 2009); Sep. 12-15, 2009. Poster F1-1991.

Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.

Wooley et al. 'Impact of renal function on the pharmacokinetics and safety of ceftolozane-tazobactam'. Antimicrob Agents Chemother. 2014 vol. 58, No. 4, pp. 2249-2255.

Sader et al. 'Post-β-Lactamase-Inhibitor Effect of Tazobactam in Combination with Ceftolozane on Extended-Spectrum-βLactamase-Producing Strains'. Antimicrob Agents Chemother. 2014 vol. 58 No. 4, pp. 2434-243.

Cabot et al. '*Pseudomonas aeruginosa* Ceftolozane-Tazobactam Resistance Development Requires Multiple Mutations Leading to Overexpression and Structural Modification of AmpC'. Antimicrob Agents Chemother. Mar. 17, 2014. [Epub ahead of print] PubMed PMID: 24637685.

Snydman et al. 'Activity of Ceftolozane/Tazobactam Against a Broad Spectrum of Recent Clinical Anaerobic Isolates'. Antimicrob Agents Chemother. 2014 vol. 58, No. 2, pp. 1218-1223.

Zhanel et al. 'Ceftolozane/Tazobactam: A Novel Cephalosporin/β-Lactamase Inhibitor Combination with Activity Against Multidrug-Resistant Gram-Negative Bacilli'. Drugs. 2014 vol. 74 No. 1, pp. 31-51.

Vanscoy et al. 'Pharmacological basis of β-lactamase inhibitor therapeutics: tazobactam in combination with Ceftolozane'. Antimicrob Agents Chemother. 2013. vol. 57 No. 12, pp. 5924-5930.

Toda et al. 'FR264205, A Novel Parenteral Antipseudomonal Cephem: Synthesis and SAR of 3-(2,4-Disubstituted 3-Aminopyrazolio)methyl Cephalosporins'. 46th Annual Interscience Conference on Antimicrobial Agents and Chemotherapy (ICAAC 2006); Sep. 27-30, 2006; San Francisco, CA. Oral Presentation F1-0240.

(56) References Cited

OTHER PUBLICATIONS

Walkty et al. 'In vitro activity of ceftolozane-tazobactam against *Pseudomonas aeruginosa* isolates obtained from patients in Canadian hospitals in the CANWARD study, 2007 to 2012'. Antimicrob Agents Chemother. 2013, vol. 57, No. 11, pp. 5707-5709.
Hong et al. 'Ceftolozane/tazobactam: a novel antipseudomonal cephalosporin and β-lactamase-inhibitor combination'. Infect Drug Resist. 2013 vol. 29, No. 6, pp. 215-223.
Zilberberg et al. 'Prevalence of multidrug-resistant *Pseudomonas aeruginosa* and carbapenem-resistant Enterobacteriaceae among specimens from hospitalized patients with pneumonia and bloodstream infections in the United States from 2000 to 2009'. J Hosp Med. 2013 vol. 8, No. 10, pp. 559-563.
Zilberberg et al. 'Secular Trends in Gram-Negative Resistance among Urinary Tract Infection Hospitalizations in the United States, 2000-2009'. Infect Control Hosp Epidemiol. 2013, vol. 34, No. 9, pp. 940-946.
Hayakawa et al. 'Epidemiology and Risk Factors for Isolation of *Escherichia coli* Producing CTX-M-Type Extended-Spectrum β-Lactamase in a Large U.S. Medical Center'. Antimicrob Agents Chemother. 2013 vol. 57, No. 8, pp. 4010-4018.
Vanscoy et al. 'Relationship between Ceftolozane/Tazobactam Exposure and Drug-Resistance Amplification in a Hollow-Fiber Infection Model'. Antimicrob Agents Chemother. Jun. 17, 2013. [Epub ahead of print] PubMed PMID: 23774429.
Vanscoy et al. 'Pharmacokinetics-Pharmacodynamics of Tazobactam in Combination with Ceftolozane in an In Vitro Infection Model'. Antimicrob Agents Chemother. 2013 vol. 57, No. 6, pp. 2809-2814.
Craig et al. 'In-Vivo Activity of Ceftolozane, a New Cephalosporin, with and without Tazobactam against *Pseudomonas aeruginosa* and Enterobacteriaceae, including Strains with Extended-Spectrum β-Lactamases, in the Thighs of Neutropenic Mice'. Antimicrob Agents Chemother. 2013 vol. 57, No. 4, pp. 1577-1582.
Jacqueline et al. 'Efficacy of ceftolozane in a murine model of *Pseudomonas aeruginosa* acute pneumonia: in vivo antimicrobial activity and impact on host inflammatory response'. J Antimicrob Chemother. 2013 vol. 63, No. 1, pp. 177-183.
Miller et al. 'CXA-201 dose selection based on probability of target attainment and drug exposure in subjects with varying degrees of renal impairment'. 51st Annual Interscience Conference on Antimicrobial Agents and Chemotherapy (ICAAC 2011); Sep. 17-20, 2011; Chicago, IL. Oral Presentation A-1099.
Titelman et al. 'In vitro activity of CXA-101 plus tazobactam against CTX-M-14- and CTX-M-15-producing *Escherichia coli* and *Klebsiella pneumoniae*'. Diagn Microbiol Infect Dis. 2011 vol. 70, No. 1, pp. 137-141.
Ge et al. 'Pharmacokinetics and safety of CXA-101, a new antipseudomonal cephalosporin, in healthy adult male and female subjects receiving single- and multiple-dose intravenous infusions'. Antimicrob Agents Chemother. 2010 vol. 54, No. 8, pp. 3427-3431.
Juan et al. 'Activity of a new antipseudomonal cephalosporin, CXA-101, against carbapenem-resistant and multidrug-resistant *Pseudomonas aeruginosa* clinical strains'. Antimicrob Agents Chemother. 2010, vol. 54, No. 2, pp. 846-851.
Sader et al. 'Antimicrobial Activity of Ceftolozane/Tazobactam Tested Against Gram-Negative Bacterial Isolates from Hospitalized Patients with Pneumonia in European Hospitals (2011)'. 23rd Annual Meeting of the European Congress of Clinical Microbiology (ECCMID 2013); Apr. 27-30, 2013; Berlin, Germany. Oral Presentation O-181.
Nicasio et al. 'PK-PD of Tazobactam (TAZ) in Combination with Piperacillin (PIP) in an In Vitro Infection Model (IVIM)'. 53rd Annual Interscience Conference on Antimicrobial Agents and Chemotherapy (ICAAC 2013); Sep. 10-13, 2013; Denver, CO. Oral Presentation.
Ambrose, et al: Pharmacokinetic-pharmacodynamic considerations in the design of hospital-acquired or ventilator-associated bacterial pneumonia studies: look before you leap!; Clin Infect Dis, 2010, vol. 51, Suppl 1, pp. 5103-S110

American Thoracic Society; Infectious Diseases Society of America; Guidelines for the management of adults with hospital-acquired, ventilator-associated, and healthcare-associated pneumonia; Am J Respir Crit Care Med., 2005, vol. 171(4), pp. 388-416.
Baughman, et al: The diagnosis and treatment challenges in nosocomial pneumonia; Diagn Microbiol Infect Dis, vol. 33(2), pp. 131-139.
Bergogne-Berezin: Predicting the efficacy of antimicrobial agents in respiratory infections: is tissue concentration valid measure?; J Antimicrob Chemother, 1995, vol. 35, pp. 363-371.
Boselli, et al: Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.
Boselli, et al: Alveolar concentrations of piperacillin/tazobactam administered in continuous infusion to patients with—associated pneumonia; Crit Care Med, 2008, vol. 36, pp. 1500-1506.
Chastre, et al: Ventilator-associated pneumonia; Am J Respir Crit Care Med, 2002, vol. 165(7), pp. 867-903.
Chastre, et al: Comparison of 8 vs 15 days of antibiotic therapy for ventilator-associated pneumonia in adults: a randomized trial; JAMA, 2003, vol. 290(19), pp. 2588-2598.
El Solh: Update on the treatment of *Pseudomonas aeruginosa* pneumonia; J Antimicrob Chemother, 2009, vol. 64, pp. 229-238.
Freire, et al: Comparison of tigecycline with imipenem/cilastatin for the treatment of hospital-acquired penumonia; Diag Microbio and Infec Dis, 2010, vol. 68, pp. 140-151.
Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.
Jones, et al: Microbial etiologies of hospital-acquired bacterial pneumonia and ventilator-associated bacterial pneumonia; Clin Infect Dis; 2010, Suppl 1, pp. S81-S87.
Joseph, et al: Ventilator-associated pneumonia: A Review; EurJ Intern Med; 2010, vol. 21(5), pp. 360-368.
Klevens, et al: Estimating health care-associated infections and deaths in U.S. hospitals, 2002; Public Health Rep, 2007, vol. 122, pp. 160-166.
Knaus, et al: APACHE II: A severity of disease classification system; Crit Care Med, 1985, vol. 13, pp. 818-829.
Komuro, et al: Inhibition of the renal excretion of tazobactam by piperacillin; J Antimicrob Chemother, 1994, vol. 34, pp. 555-564.
Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).
Mesaros, et al: *Pseudomonas aeruginosa*: resistance and therapeutic options at the turn of the new millennium; Clin Microbiol Infect, 2007, vol. 13, pp. 560-578.
Occhipinti, et al: Pharmacokinetics and pharmacodynamics of two multiple-dose piperacillin-tazobactam regimens; Antimicrob Agents Chemother, 1997, vol. 41, pp. 2511-2517.
Pankey: Tigecycline; J Antimicrob Chemotherapy, 2005, vol. 56, pp. 470-480.
Pea: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.
Richards, et al: Nosocomial infections in medical intensive care units in the United States. National Nosocomial Infections Surveillance System; Crit Care Med, 1999, Vol .27(5), pp. 887-892.
Schulgen, et al: Estimation of extra hospital stay attributable to nosocomial infections: heterogeneity and timing of events; J Clin Epidemiol; Apr. 2000, vol. 53(4), pp. 409-417.
Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.
Udy, et al: Augmented renal clearance: implications for antibacterial dosing in the critically ill; Clin Pharmacokinet, 2010, vol. 49(1), pp. 1-16.

(56) References Cited

OTHER PUBLICATIONS

Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.
Wunderink, et al: Linezolid in methicillin-resistant *Staphylococcus aureus* nosocomial pneumonia: a randomized, controlled study; Clin Infect Dis, 2012, vol. 54(5), pp. 621-629.
Zilberberg, et al: Epidemiology of healthcare-associated pneumonia (HCAP); Semin Respir Crit Care Med, 2009, vol. 30, pp. 10-15.
Zosyn®. Prescribing Information. Wyeth Pharmaceuticals, Inc., Philadelphia, PA, USA; http://labeling.pfizer.com/showlabeling. aspx?id=416 (Apr. 23, 2012, date last accessed), 26 pages.
Non-Final Office Action issued for U.S. Appl. No. 14/214,234, mailed Jul. 7, 2014 (16 pages).
Arin et al, 'The Comparative Stability of Different Types of Penicillin and Cephalosporin N-pyrryl derivatives'. Pharmazie 1988, vol. 43, pp. 18-19.
Cefazolin, (For Injection USP) Approved Dec. 1988, Product Label, B. Braun Medical Inc. Revised Jan. 2012.
Ceftazidime, (Systemic) Approved Nov. 1985, Product Label. American Society of Health-System Pharmacists Inc. 2004.
Claforan, (Sterile—Cefotaxime for injection, USP & Injection—Cefotaxime injection) Approved Prior to Jan. 1982, Product Label. Sanofi-Aventis U.S. LLC 2011.
Cubist Pharmaceuticals, 'Cubist Announces Positive Results from Two Phase 2 Trials, CXA-201 and CDAD Program'. Cubist Press Release. Jun. 2011.
Doribax, Approved Oct. 2007, Product Label. Ortho-McNeil-Janssen Pharmaceuticals, Inc. 2007.
Fortaz, (ceftazidime for Injection) (Ceftazidime Injection) Approved Jul. 1985, Product Label. GlaxoSmithKline 2007.
Maxipime, (Cefepime Hydrochloride, USP) Approved Jan. 1996, Product Label. Bristol-Myers Squibb Company, Revised Mar. 2009.
Yamana et al, 'Comparative Stability of Cephalosporins in Aqueous Solution: Kinetics and Mechanisms of Degradation'. Journal of Pharmaceutical Sciences 1976, vol. 65, No. 11, pp. 1563-1574.
Rocephin, (Ceftiaxone Sodium) Approved Aug. 1993, Product Label. Roche Laboratories, Copyright 1998.
Zithromax, (azithromycin injection) Approved Sep. 1994, Product Label. Pfizer Labs, Revised Feb. 2013.
Teflaro, (Ceftaroline fosamil) Approved Oct. 2010, Product Label. Forst Laboratories, Inc. 2010.
Non-Final Office Action for U.S. Appl. No. 14/251,372, dated Sep. 5, 3014, 19 pages.
Non-Final Office Action issued for U.S. Appl. No. 14/214,324, mailed Jul. 7, 2014 (16 pages).

Miller et al. 'Pharmacokinetics and Safety of Intravenous Ceftolozane-Tazobactum in Healthy Adult Subjects following Single and Multiple Ascending Doses'. Antimicrobial Agents and Chemotherapy. 2012. vol. 56, No. 6, pp. 3086-3091.
Lehr et al. 'Particulate Matter Contamination of Intravenous Antibiotics Aggravates Loss of Functional Capillary Density in Postischemic Striated Muscle'. Am. J. Respir. Crit. Care Med. 2002, vol. 165, pp. 514-520.
U.S. Appl. No. 14/250,879, filed May 22, 2014, 74 pages.
Office Action issued for U.S. Appl. No. 14/250,879. Dated Jul. 8, 2014. 40 pages.
Extended European Search Report for Application No. 14160151.8, dated May 13, 2014, 9 pages.
Notification of Transmittal of the International Search Report and the Written Opinion of the International Searching Authority for International Application No. PCT/US2014/028642, Dated Aug. 7, 2014, 14 pages.
U.S. Appl. No. 14/020,230, filed Sep. 6, 2013.
U.S. Appl. No. 14/020,212, filed Sep. 6, 2013.
U.S. Appl. No. 14/200,383, filed Mar. 14, 2014.
U.S. Appl. No. 14/211,216, filed Mar. 14, 2014.
U.S. Appl. No. 14/211,229, filed Mar. 14, 2014.
U.S. Appl. No. 14/211,465, filed Mar. 14, 2014.
U.S. Appl. No. 14/211,526, filed Mar. 14, 2014.
U.S. Appl. No. 14/212,781, filed Mar. 14, 2014.
U.S. Appl. No. 14/214,212, filed Mar. 14, 2014.
U.S. Appl. No. 14/214,324, filed Mar. 14, 2014.
U.S. Appl. No. 14/213,532, filed Mar. 14, 2014.
U.S. Appl. No. 14/212,590, filed Mar. 14, 2014.
U.S. Appl. No. 14/214,221, filed Mar. 14, 2014.
U.S. Appl. No. 14/214,417, filed Mar. 14, 2014.
U.S. Appl. No. 14/214,367, filed Mar. 14, 2014.
U.S. Appl. No. 14/213,997, filed Mar. 14, 2014.
U.S. Appl. No. 14/212,625, filed Mar. 14, 2014.
U.S. Appl. No. 14/214,260, filed Mar. 14, 2014.
Cubist Pharmaceuticals, Corporate Presentation, Sep. 2011. 'Forward Looking Statement and Non-GAAP Financial Measure Disclosure.' (1 page). a. Slide 38.
Cubist Pharmaceuticals, Corporate Presentation, Feb. 26, 2010. 'Forward Looking Statement and Non-GAAP Financial Measure Disclosure.' (1 page). a. slide 39.
Cubist Pharmaceuticals, "Cubist Pharmaceuticals to Acquire Calixa Therapeutics," Dec. 14, 2009, Available Online at http://investors.cubist.com/Mobile/file.aspx?IID=4093793&FID=8747721 (4 pages).
Shelley, S., "The Struggle to Get Anti-Infectives on a Faster Track to Commercialization," Jan. 4, 2011, Available Online at http://pharmaceuticalcommerce.com/index.php?pg=special_report&articleid=2316 (5 pages).

* cited by examiner

Figure 3

Table 1

| Impurity | RRT |
|---|---|
| Peak 1 (P1) [1] | ~0.1 |
| Peak 2 (P2) | ~0.2 |
| Peak 3 (P3) | ~0.4 |
| Peak 4 (P4) | ~0.6 |
| Peak 5 (P5) | ~0.9 |
| CXA-101 [2] | 1.0 |
| Peak 6 (P6) | ~1.1 |
| Peak 7 (P7) | ~1.3 |
| Peak 8 (P8) | ~1.4 |
| Peak 9 (P9) | ~1.7 |
| Peaks 10, 11 (P10, 11) | ~2.3 |

1. The absolute retention time for Peak 1 is 3.5 minutes.
2. The absolute retention time for CXA-101 (ceftolozane) is 24 minutes.

Figure 4B

Table 2: Compositions of Co-lyophilization Drug Product.

| Component | Function | Amount (mg/vial) |
|---|---|---|
| CXA-101 | Active pharmaceutical ingredient | 1000 (potency) |
| L-arginine | Alkalization reagent | 587 |
| Citric acid (anhydrous) | Buffer | 21 |
| Sodium chloride | Stabilizer | 476 |
| Tazobactam (free acid) | Active pharmaceutical ingredient | 500 |
| Sodium bicarbonate | Alkalization reagent | Quantity sufficient[1] for pH 4.8 to 7.0 |
| water | Dissolution solvent | Not more than 4% by HPLC[2] |
| Nitrogen | Inert gas | Sufficient quantity |

1. Sodium content is approximately 78 mg/g of tazobactam in drug product after lyophilization.
2. Water is removed during the lyophilization process and is controlled at no more than 4% by weight.

Figure 5

Table 3

| Test | Acceptance Limits (expected value) | Results | | | |
|---|---|---|---|---|---|
| | | Sampling | 60 minute | 120 minute | 180 minute |
| Content: Ceftolozane[1] | 30.4%-37.2% | 1 | 34.24 | 34.07 | 34.42 |
| | | 2 | 34.62 | 34.21 | 34.66 |
| | | 3 | 34.71 | 34.60 | 34.85 |
| | | Mean[3] | 34.52 | 34.30 | 34.64 |
| | | RSD% | 0.72 | 0.80 | 0.63 |
| Content: Tazobactam[2] | 15.2%-18.6% | 1 | 17.96 | 18.20 | 17.12 |
| | | 2 | 16.90 | 18.26 | 16.51 |
| | | 3 | 17.27 | 16.93 | 17.02 |
| | | Mean[3] | 17.38 | 17.80 | 16.89 |
| | | RSD% | 3.10 | 4.22 | 1.96 |
| Ratio of Content (w/w) ceftolozane/tazobactam | 2.00[4] | 1 | 1.91 | 1.87 | 2.01 |
| | | 2 | 2.05 | 1.87 | 2.10 |
| | | 3 | 2.01 | 2.04 | 2.05 |
| | | Mean[3] | 1.99 | 1.93 | 2.05 |
| | | RSD% | 3.69 | 5.12 | 2.2 |

RSD = relative standard deviation

[1] Theoretical value: 33.96% Acceptance limits are 90% - 110% of the theoretical value.

[2] Theoretical value: 16.99% Acceptance limits are 90% - 110% of the theoretical value.

[3] Three samples are taken at each time point at three places to measure the percentage by weight of ceftolozane and tazobactam. The "Mean" is the average of the percentages or the weight ratios of Ceftolozane/tazobactam.

[4] Acceptance limits were established based on batch history.

Figure 6

Table 4: Formulation composition of the Co-Lyo Combo Drug Product.

| | | |
|---|---|---|
| CXA-201 Comp. | 16.3 g active | ceftolozane |
| | 8.1 g active | Tazobactam free ac. |
| | 15.5 g | L-Arginine |
| | 350 mg | Citric acid |
| | 7.9 g | NaCl |
| | 6.1 | pH compounded solution |

Figure 7A

Table 5: Stability data Co-Lyo Combo Drug Product at 25 °C.

| Test items | Spec. D.P. | T0 | T1 25°C | T2 25°C |
|---|---|---|---|---|
| Related Substances | | | | |
| -Peak1 | ≤ 1.50% | 0.31% | 0.54% | 0.71% |
| -Peak2 | ≤ 0.40% | 0.07% | 0.07% | 0.09% |
| -Peak3 | ≤ 0.30% | <0.03% | <0.03% | <0.03% |
| -Peak4 | ≤ 0.80% | 0.08% | 0.08% | 0.09% |
| -Peak5 | ≤ 1.00% | 0.27% | 0.26% | 0.29% |
| -Peak6 | ≤ 0.15% | <0.03% | <0.03% | <0.03% |
| -Peak7 | ≤ 2.00% | 0.64% | 0.65% | 0.66% |
| -Peak8 | ≤ 0.15% | <0.03% | <0.03% | <0.03% |
| -Peak9 | ≤ 0.60% | 0.05% | 0.11% | 0.10% |
| -Peak10,11 | ≤ 0.15% each | 0.04% | 0.04% | 0.04% |
| -Peak12 | ≤ 2.00% | <0.03% | <0.03% | <0.03% |
| Others (RRT 0.43) | ≤ 0.15% | <0.03% | <0.03% | 0.04% |
| Others (RRT 1.22) | ≤ 0.15% | 0.13% | 0.30% | 0.38% |
| Others (RRT 2.18) | ≤ 0.15% | 0.03% | <0.03% | 0.05% |
| Others (RRT 2.77) | ≤ 0.15% | <0.03% | 0.03% | 0.03% |
| Sing. Unk. | ≤ 0.15% | 0.05% | 0.07% | 0.05% |
| Total | ≤ 5.00% | 1.67% | 2.19% | 2.77% |
| pH | report value | 5.5 | | 4.83 |

Figure 7B
Table 6: Stability data Co-Lyo Combo Drug Product at 40 °C.

| Test items | Spec. D.P. | T0 | T1 40°C | T2 40°C |
|---|---|---|---|---|
| Related Substances | | | | |
| -Peak1 | ≤ 1.50% | 0.31% | 1.77% | 2.22% |
| -Peak2 | ≤ 0.40% | 0.07% | 0.10% | 0.16% |
| -Peak3 | ≤ 0.30% | <0.03% | <0.03% | 0.06% |
| -Peak4 | ≤ 0.80% | 0.08% | 0.09% | 0.09% |
| -Peak5 | ≤ 1.00% | 0.27% | 0.27% | 0.30% |
| -Peak6 | ≤ 0.15% | <0.03% | <0.03% | <0.03% |
| -Peak7 | ≤ 2.00% | 0.64% | 0.69% | 0.78% |
| -Peak8 | ≤ 0.15% | <0.03% | <0.03% | 0.10% |
| -Peak9 | ≤ 0.60% | 0.05% | 0.09% | 0.09% |
| -Peak10,11 | ≤ 0.15% each | 0.04% | 0.04% | 0.05% |
| -Peak12 | ≤ 2.00% | <0.03% | <0.03% | <0.03% |
| Others (RRT 0.43) | ≤ 0.15% | <0.03% | 0.09% | 0.15% |
| Others (RRT 1.22) | ≤ 0.15% | 0.13% | 0.74% | 0.97% |
| Others (RRT 2.18) | ≤ 0.15% | 0.03% | <0.03% | 0.08% |
| Others (RRT 2.77) | ≤ 0.15% | <0.03% | <0.03% | 0.04% |
| Sing. Unk. | ≤ 0.15% | 0.05% | 0.11% | 0.25% |
| Total | ≤ 5.00% | 1.67% | 4.49% | 6.32% |
| pH | report value | 5.5 | | 4.09 |

Figure 8

Table 7: Formulation composition of the blend Drug Product.

| | Component | Composition | Quantity as active components |
|---|---|---|---|
| CXA-201 Comp. | CXA-101 for Injection Bulk (25 g) | CXA-101 | 10.8 g |
| | | L-Arginine | 6.7 g |
| | | Citric acid | 233 mg |
| | | Sodium chloride | 5.2 g |
| | Tazobactam sodium sterile Bulk (6 g) | | 5.4 g (as Tazo free acid) |

Figure 9A

Table 8: Stability data of Blending Combo Drug Product at 25 °C/RH=60%.

| Test items | Specifications | T0 | T1 25°C | T2 25°C |
|---|---|---|---|---|
| Related Substances | | | | |
| -Peak1 | ≤ 1.50% | 0.61% | 0.93% | 1.08% |
| -Peak2 | ≤ 0.40% | <0.03% | <0.03% | <0.03% |
| -Peak3 | ≤ 0.30% | <0.03% | <0.03% | <0.03% |
| -Peak4 | ≤ 0.80% | 0.03% | 0.03% | 0.04% |
| -Peak5 | ≤ 1.00% | 0.09% | 0.12% | 0.13% |
| -Peak6 | ≤ 0.15% | <0.03% | <0.03% | <0.03% |
| -Peak7 | ≤ 2.00% | 1.28% | 1.34% | 1.35% |
| -Peak8 | ≤ 0.15% | <0.03% | <0.03% | <0.03% |
| -Peak9 | ≤ 0.60% | 0.03% | <0.03% | 0.03% |
| -Peak10,11 | ≤ 0.30% | <0.03% | 0.04% | 0.05% |
| Sing. Unk. | ≤ 0.15% | 0.13% | 0.13% | 0.14% |
| Total | ≤ 5.00% | 2.49% | 3.03% | 3.28% |
| Assay CXA-101 | Teor. %=32.6% | 32.5% | n.a. | n.a. |
| Assay Tazobactam | Teor. %=17.4% | 18.2% | n.a. | n.a. |
| Tazobactam Related Compound A | ≤ 4.0% | 0.07% | 0.12% | 0.14% |
| K.F. | ≤ 4.0% | 2.6% | n.a. | n.a. |
| pH | 5.0-7.0 | 6.0 | 5.6 | 5.1 |

Figure 9B

Table 9: Stability data of Blending Combo Drug Product at 40 °C/RH=75%.

| Test items | Specifications | T0 | T1 40°C | T2 40°C |
|---|---|---|---|---|
| Related Substances | | | | |
| -Peak1 | ≤ 1.50% | 0.61% | 1.66% | 2.28% |
| -Peak2 | ≤ 0.40% | <0.03% | <0.03% | <0.03% |
| -Peak3 | ≤ 0.30% | <0.03% | <0.03% | 0.04% |
| -Peak4 | ≤ 0.80% | 0.03% | 0.04% | 0.05% |
| -Peak5 | ≤ 1.00% | 0.09% | 0.13% | 0.14% |
| -Peak6 | ≤ 0.15% | <0.03% | <0.03% | <0.03% |
| -Peak7 | ≤ 2.00% | 1.28% | 1.41% | 1.46% |
| -Peak8 | ≤ 0.15% | <0.03% | <0.03% | <0.03% |
| -Peak9 | ≤ 0.60% | 0.03% | <0.03% | 0.03% |
| -Peak10,11 | ≤ 0.30% | <0.03% | 0.08% | 0.09% |
| Sing. Unk. | ≤ 0.15% | 0.13% | 0.14% | 0.13% |
| Total | ≤ 5.00% | 2.49% | 4.21% | 5.27% |
| Assay CXA-101 | Teor. %=32.6% | 32.5% | n.a. | n.a. |
| Assay Tazobactam | Teor. %=17.4% | 18.2% | n.a. | n.a |
| Tazobactam Related Compound A | ≤ 4.0% | 0.07% | 0.35% | 0.54% |
| K.F. | ≤ 4.0% | 2.6% | n.a. | n.a. |
| pH | 5.0-7.0 | 6.0 | 5.0 | 4.4 |

CEFTOLOZANE-TAZOBACTAM PHARMACEUTICAL COMPOSITIONS

CROSS-REFERENCE TO RELATED APPLICATIONS

This application is a continuation of U.S. patent application Ser. No. 14/214,212, filed Mar. 14, 2014, which claims priority to U.S. Provisional Patent Application No. 61/792,092, filed Mar. 15, 2013, and U.S. Provisional Patent Application No. 61/793,007, filed Mar. 15, 2013, both of which are incorporated herein in their entirety.

TECHNICAL FIELD

This disclosure relates to antibacterial compositions comprising ceftolozane and tazobactam.

BACKGROUND

The pharmaceutical antibiotic composition comprising ceftolozane and tazobactam in a 2:1 weight ratio of ceftolozane active to tazobactam active ("CXA-201") displays potent antibacterial activity, including antibiotic activity against infections caused by many Gram-negative pathogens such as *Pseudomonas aeruginosa* (*P. aeruginosa*), *Escherichia coli* (*E. coli*), *Klebsiella pneumonia* (*K. pneumonia*). In particular, CXA-201 is a pharmaceutical composition useful for intravenous administration for the treatment of complicated intra-abdominal infections and/or complicated urinary tract infections, and is being evaluated for treatment of pneumonia.

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. The antibacterial activity of ceftolozane is believed to result from its interaction with penicillin binding proteins (PBPs) to inhibit the biosynthesis of the bacterial cell wall which acts to stop bacterial replication. Ceftolozane sulfate is a pharmaceutically acceptable ceftolozane salt of formula (I) that can be formulated for intravenous administration or infusion.

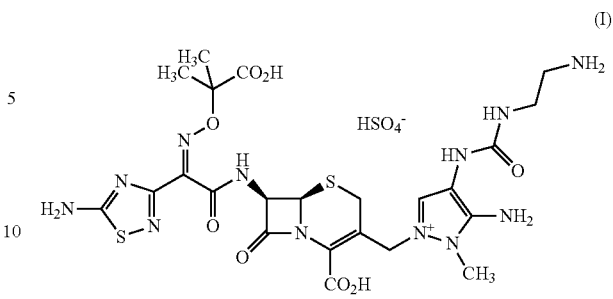

(I)

In CXA-201, ceftolozane is combined with the β-lactamase inhibitor ("BLI") tazobactam. Tazobactam is a BLI against Class A and some Class C β-lactamases, with well-established in vitro and in vivo efficacy in combination with active β-lactam antibiotics. Tazobactam can be combined with ceftolozane as a free acid tazobactam form of formula (II).

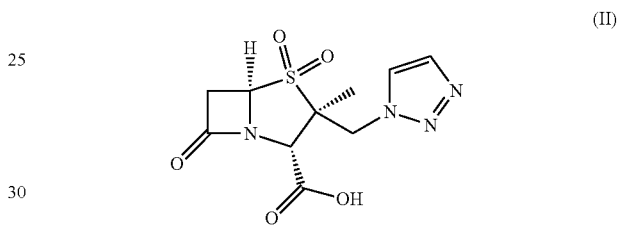

(II)

Pharmaceutical compositions comprising one or more drug substances can be prepared by lyophilization of a solution containing the drug substance(s). Lyophilization is a process of freeze-drying in which water is sublimed from a frozen solution of one or more solutes. Specific methods of lyophilization are described in Remington's Pharmaceutical Sciences, Chapter 84, page 1565, Eighteenth Edition, A. R. Gennaro, (Mack Publishing Co., Easton, Pa., 1990). It has now been found and reported herein that compositions formed by lyophilizing ceftolozane and tazobactam through co-lyophilization, (i.e., the ceftolozane and tazobactam were combined and lyophilized together in Example 3, as opposed to separately) resulted in the formation of significant amounts of an undesired by-product represented by formula (III) (See Example 5 and the results reported in Tables 5 and 6 in FIGS. 7A and 7B).

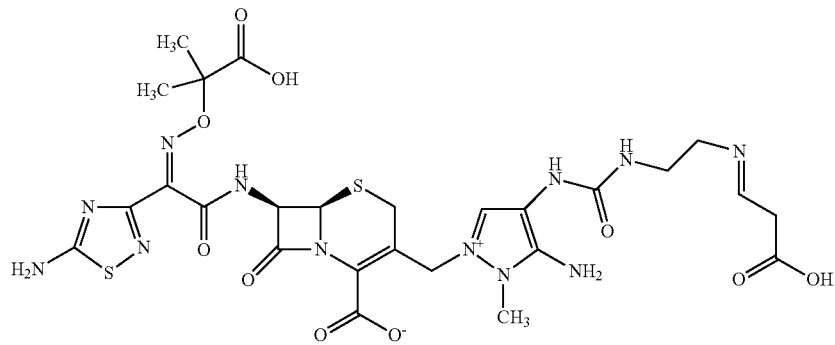

(III)

Therefore, there remains a need for compositions comprising ceftolozane and/or tazobactam with reduced or even undectable amounts (e.g., less than about 0.03% by high performance liquid chromatography, or "HPLC") of the compound of formula (III) and methods for manufacturing these compositions.

SUMMARY

Applicants have discovered pharmaceutical compositions comprising ceftolozane and tazobactam with reduced and even undetectable amounts of the compound of Formula (III), and methods of manufacturing these compositions. The invention is based in part on the discovery that the formation of the compound represented by Formula (III) can be reduced if not completely suppressed by lyophilizing ceftolozane in the absence of tazobactam and then blending the lyophilized ceftolozane with a dry tazobactam composition, such as a tazobactam composition lyophilized in the absence of ceftolozane (See Example 6 and the results reported in Tables 8 and 9 in FIGS. 9A and 9B). Based on these results, pharmaceutical compositions comprising ceftolozane and tazobactam, and pharmaceutical compositions prepared using ceftolozane and tazobactam are provided herein. In particular, these pharmaceutical compositions can include ceftolozane and/or tazobactam with reduced or even undetectable amounts of a compound of formula (III).

HPLC; or even undectable amounts (e.g., less than about 0.03% by HPLC) of a compound of formula (III) detectable at a retention time relative to ceftolozane of 1.22 by high performance liquid chromatography (HPLC) using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C. (hereinafter referred to as the "method of Example 2").

CXA-201 compositions comprising less than about 0.15%, 0.10%, 0.05% or 0.03% by weight; or from 0.03-0.05%, 0.03-0.1% or 0.03-0.15% by HPLC of the compound of formula (III) can be obtained by a process comprising the steps of: (a) forming a first aqueous solution comprising ceftolozane (e.g., in a pharmaceutically acceptable salt such as formula (I)), (b) lyophilizing the first aqueous solution to obtain a lyophilized ceftolozane composition, and (c) blending the lyophilized ceftolozane composition with a tazobactam composition (e.g., tazobactam acid lyophilized in the absence of ceftolozane) in an amount that provides a 2:1 weight ratio between the amount of ceftolozane active and tazobactam active.

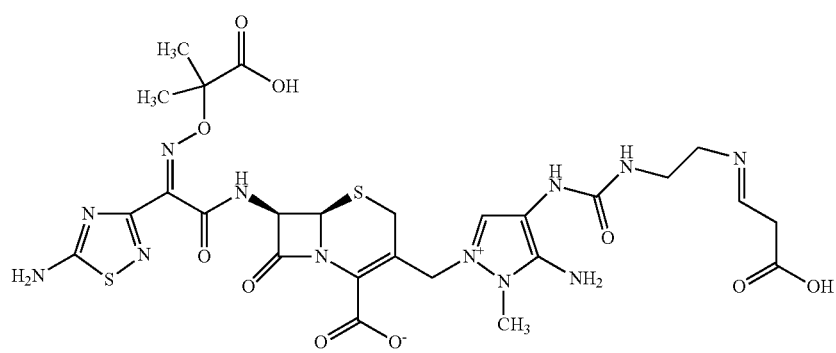

(III)

In one embodiment, a pharmaceutical composition can include ceftolozane and tazobactam with less than 0.15%, 0.10%, 0.05% or 0.03% by weight; or from 0.03-0.05%, 0.03-0.1% or 0.03-0.15% by HPLC or even undectable amounts of the compound of formula (III) (e.g., less than about 0.03% of the compound of Formula (III) measured by HPLC). These pharmaceutical compositions can be obtained by a process comprising the steps of (a) lyophilizing ceftolozane in the absence of tazobactam to obtain a lyophilized ceftolozane composition; and (b) combining the lyophilized ceftolozane with tazobactam under conditions suitable to obtain said pharmaceutical composition with the aforementioned purity levels. The combination of the lyophilized ceftolozane composition with tazobactam can include blending the lyophilized ceftolozane composition with lyophilized or crystalline tazobactam material.

In one aspect, provided herein is a pharmaceutical composition comprising a blend of separately lyophilized tazobactam and ceftolozane sulfate in an amount providing 1,000 mg of ceftolozane active per 500 mg of tazobactam active, further comprising less than 0.15%, 0.10%, 0.05% or 0.03% by weight; from 0.03-0.05%, 0.03-0.1% or 0.03-0.15% by of Example 1. The chromatograms were obtained according to the analytical method described in Example 2.

Figure 2:
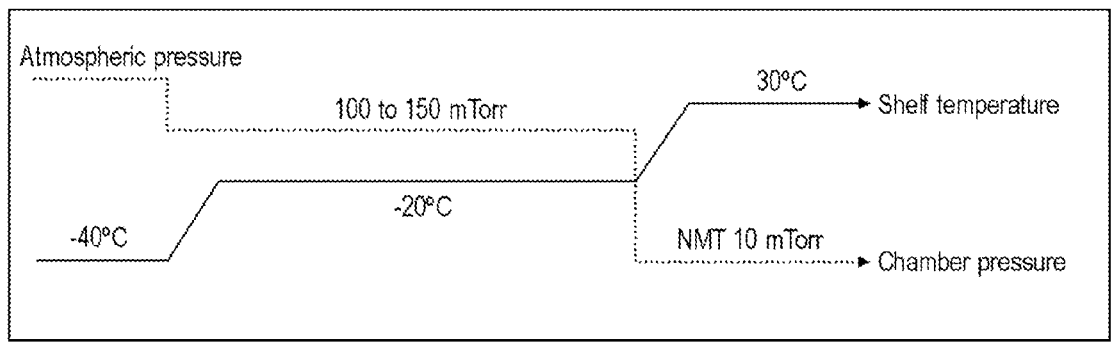

FIG. 2 is a diagram of a lyophilization process for the ceftolozane obtained according to the process described in Example 1.

FIG. 3 is a table (Table 1) of peaks for the ceftolozane prepared by the lyophilization process in Example 1 obtained by HPLC according to the analytical method of Example 2.

Figure 4A:
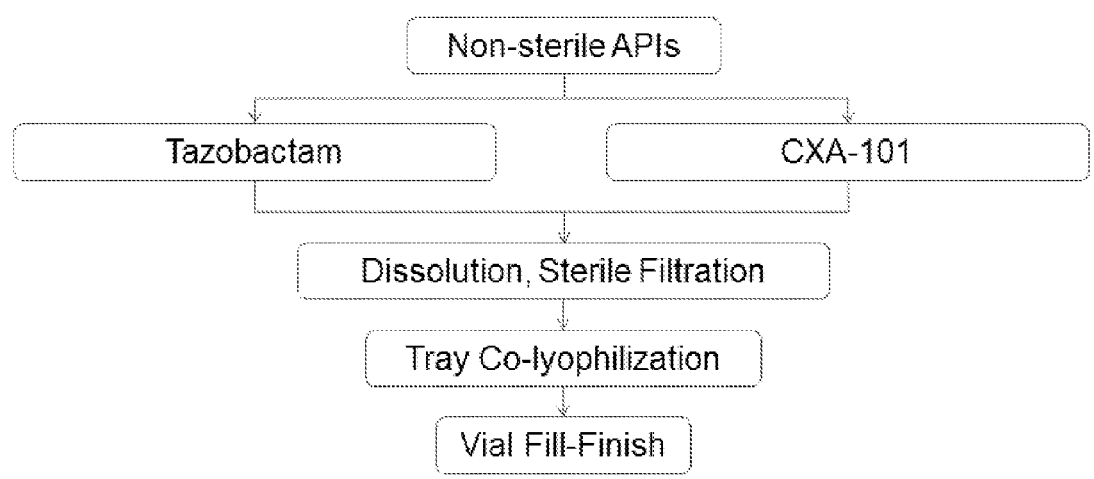

FIG. 4A is a schematic showing a process for making the compound of formula (III) with ceftolozane and tazobactam.

FIG. 4B is a table (Table 2) showing a first composition that can be lyophilized to form a composition comprising the compound of formula (III).

FIG. 5 is a table (Table 3) showing in-process testing of blending samples of bulk drug product at five places.

FIG. 6 is a table (Table 4) of the composition of the formulation used to prepared the Co-Lyophilized Combo drug product used in Example 5.

FIG. 7A is a table (Table 5) of the impurity composition of the Co-Lyophilized Combo drug product at $T_0$ (time zero), $T_1$ (one month) and $T_2$ (three months) after being maintained at 25° C./60% relative humidity.

FIG. 7B is a table (Table 6) of the impurity composition of the Co-Lyophilized Combo drug product at $T_0$ (time zero), $T_1$ (one month) and $T_2$ (three months) after being maintained at 40° C./75% relative humidity.

FIG. 8 is a table (Table 7) of the composition of the formulation used to prepare the Blended Combination drug product used in Example 6.

FIG. 9A is a table (Table 8) of the impurity composition of the Blended Combination drug product at $T_0$ (time zero), $T_1$ (one month) and $T_2$ (three months) after being maintained at 25° C./60% relative humidity.

FIG. 9B is a table (Table 9) of the impurity composition of the Blended Combination drug product at $T_0$ (time zero), $T_1$ (one month) and $T_2$ (three months) after being maintained at 40° C./75% relative humidity.

DETAILED DESCRIPTION

Pharmaceutical compositions comprising ceftolozane and tazobactam with reduced or even undetable levels of the compound of formula (III) (e.g., including levels of compound of formula (III) that are not detectable by HPLC according to Example 2 and/or comprise less than 0.15%, 0.10%, 0.05% or 0.03% by weight; or from 0.03-0.05%, 0.03-0.1% or 0.03-0.15% by HPLC according to Example 2) can be obtained by blending a first composition comprising a therapeutically effective amount of ceftolozane in the absence of tazobactam with a second composition comprising a therapeutically effective amount of tazobactam in the absence of ceftolozane to form a blended pharmaceutical composition.

The (first) ceftolozane composition can be prepared in the absence of tazobactam by forming a first aqueous solution comprising ceftolozane sulfate and other components including excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust the aqueous solution to a pH of 5-7 (e.g., to pH 6-7) and to increase the solubility of ceftolozane; and citric acid is used to prevent discoloration of the product, due to its ability to chelate metal ions. In one embodiment, the pH of the first aqueous solution is suitable for making an injectable product (e.g,, a pH range of 5-7, including 6-7). Preferably, the first aqueous solution comprises about 125 mg-500 mg sodium chloride per 1,000 mg of ceftolozane active. The ceftolozane can be included as an amount of ceftolozane sulfate of formula (I) containing at least about 1,000 mg ceftolozane active. The (first) aqueous solution is then lyophilized to form a first lyophilized ceftolozane composition, which is combined with tazobactam, e.g., the lyophilized tazobactam (e.g., lyophilized tazobactam sodium) or crystalline tazobactam The (second) tazobactam composition can be prepared in the absence of ceftolozane by forming a second solution comprising tazobactam. The tazobactam can be included in an amount providing about 500 mg of tazobactam active per 1,000 mg ceftolozane active (i.e., a 1:2 weight ratio of tazobactam active to ceftolozane active). Tazobactam is a β-lactamase inhibitor of the structure of formula (II) in its free acid form.

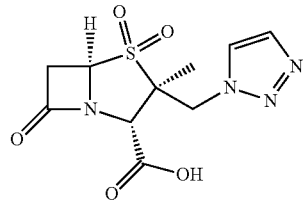

Unless otherwise indicated, tazobactam can be a free acid, a sodium salt, an arginine salt, or a hydrate or solvate thereof. In one embodiment, the tazobactam in the (second) tazobactam composition is tazobactam acid and the second composition further comprises sodium bicarbonate or sodium hydroxide. Lyophilizing tazobactam in the presence of sodium bicarbonate or sodium hydroxide forms a lyophilized tazobactam sodium, which can then be further blended with the (first) lyophilized ceftolozane composition.

Pharmaceutical compositions with reduced or undetable amounts of the compound of formula (III) can be obtained by lyophilizing ceftolozane without formylacetic acid and/or tazobactam under conditions that prevent formation of the compound of formula (III) (e.g., Example 1 and 4). The presence of a compound of formula (III) can be detected by HPLC (e.g., Examples 2, 5 and 6). Specific methods of lyophilization are described in Example 1 and Remington's Pharmaceutical Sciences, Chapter 84, page 1565, Eighteenth Edition, A. R. Gennaro, (Mack Publishing Co., Easton, Pa., 1990). The formation of the compound of formula (III) can be avoided by preventing the reaction of ceftolozane and formylacetic acid. In one embodiment, the compound of formula (III) can be suppressed by separately lyophlizing ceftolozane sulfate and tazobactam in separate solutions, and then blending the lyophilized compositions to form a pharmaceutical composition.

In one aspect, antibiotic pharmaceutical compositions comprising ceftolozane and tazobactam with less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing ceftolozane in the absence of tazobactam to obtain a lyophilized ceftolozane composition, and (b) blending the lyophilized ceftolozane composition with a composition comprising tazobactam under conditions suitable for attaining the aforementioned purity levels, e.g., by blending with crystalline tazobactam or lyophilized tazobactam.

In another aspect, antibiotic pharmaceutical compositions comprising ceftolozane and tazobactam and less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing tazobactam in the absence of ceftolozane to obtain a lyophilized tazobactam composition, and (b) blending the lyophilized tazobactam composition with a composition comprising ceftolozane (e.g., lyophilized ceftolozane sulfate).

In a third aspect, antibiotic pharmaceutical compositions comprising ceftolozane and tazobactam and less than about 0.15%, 0.10%, 0.05% or 0.03% by weight; or from 0.03-0.05%, 0.03-0.1% or 0.03-0.15% by HPLC of the compound of formula (III) are obtained by a process comprising the steps of: (a) lyophilizing tazobactam in the absence of ceftolozane to obtain a lyophilized tazobactam composition, (b) lyophilizing ceftolozane in the absence of tazobactam to obtain a lyophilized ceftolozane composition, and (c) blending the lyophilized tazobactam composition with the lyophilized ceftolozane composition.

Pharmaceutical compositions comprising the compound of formula (III), ceftolozane and tazobactam can be formulated to treat infections by parenteral administration (including subcutaneous, intramuscular, and intravenous) administration. Pharmaceutical compositions may additionally comprise excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH and to increase the solubility of ceftolozane; and citric acid is used to prevent discoloration of the product, due to its ability to chelate metal ions. In one particular embodiment, the pharmaceutical compositions described herein are formulated for administration by intravenous injection or infusion.

Other pharmaceutical antibiotic compositions can include ceftolozane sulfate and the compound of formula (III). For example, pharmaceutical compositions comprising 0.13%, 0.15%, 0.30%, 0.38%, 0.74% or 0.97% of the compound of formula (III) are herein. The pharmaceutical antibiotic compositions can be provided in a unit dosage form (e.g., in a vial). The unit dosage form can be dissolved with a pharmaceutically acceptable carrier, and then intravenously administered. The unit dosage form comprises 1000 mg of ceftolozane active and 500 mg tazobactam, typically 1000 mg ceftolozane active as ceftolozane sulfate and 500 mg of tazobactam active as tazobactam sodium, argininate or free acid. The unit dosage forms are commonly stored in vials.

In one aspect, provided herein is a unit dosage form container (e.g., a bag, vial or the like) containing a unit dosage form of a pharmaceutical composition formulated for parenteral administration for the treatment of complicated intra-abdominal infections or complicated urinary tract infections, the pharmaceutical composition comprising a therapeutically effective amount of ceftolozane sulfate and tazobactam in a ratio of 1,000 mg ceftolozane active per 500 mg of tazobactam active, the pharmaceutical composition obtained by a process comprising the steps of:
  a. lyophilizing a first aqueous solution in the absence of tazobactam, the first aqueous solution comprising ceftolozane sulfate, 125 mg to 500 mg of sodium chloride per 1,000 mg of ceftolozane active, L-arginine and/or citric acid in an amount effective to adjust the pH of the first aqueous solution to 5-7 (e.g., 6-7) prior to lyophilization to obtain a first lyophilized ceftolozane composition,
  b. lyophilizing a second solution in the absence of ceftolozane, the second solution comprising tazobactam being lyophilized to form a second lyophilized tazobactam composition; and 'c. blending the first lyophilized ceftolozane composition and the second lyophilized tazobactam composition to obtain a blended pharmaceutical composition in the unit dosage form.

In one embodiment of the unit dosage form container, the tazobactam in the second solution is tazobactam acid, and wherein the tazobactam acid in the second solution is lyophilized in the presence of sodium bicarbonate or sodium hydroxide, thereby forming lyophilized tazobactam sodium in the second lyophilized tazobactam solution. A pharmaceutical composition can include ceftolozane sulfate and tazobactam in an amount providing 1,000 mg of ceftolozane active per 500 mg of tazobactam active, and 0.03% to 0.15% by HPLC of a compound of formula (III) detectable at a retention time relative to ceftolozane of 1.22 by high performance liquid chromatography using a Develosil column ODS-UG-5; 5 micrometers; 250×4.6 mm, a mobile phase of sodium perchlorate buffer solution (pH 2.5)/CH$_3$CN 90:10 (v/v) at a 1.0 mL/min flow rate and oven temperature of 45° C. Optionally, the pharmaceutical composition can further include 125 mg to 500 mg of sodium chloride per 1,000 mg of ceftolozane active, and L-arginine. The tazobactam in the composition can be tazobactam sodium.

The pharmaceutical compositions provided herein comprising ceftolozane sulfate and tazobactam in a ratio of 1,000 mg ceftolozane active per 500 mg of tazobactam active, can be obtained by a process comprising the steps of:
  a. lyophilizing a first aqueous solution in the absence of tazobactam, the first aqueous solution comprising ceftolozane sulfate at a pH of 5-7 (e.g, 6-7) prior to lyophilization to obtain a first lyophilized ceftolozane composition,
  b. blending the first lyophilized ceftolozane composition with tazobactam to obtain an antibacterial composition.

The pharmaceutical compositions can be administered for the treatment of infections, such as complicated intra-abdominal infections, complicated urinary tract infections (cUTIs) and pneumonia (e.g., community-acquired, hospital-acquired, etc). In one aspect, provided herein is a method for the treatment of bacterial infections in a mammal, comprising administering to said mammal a therapeutically effective amount of a pharmaceutical composition prepared according to the methods described herein. A method for the treatment of bacterial infections in a mammal can comprise administering to said mammal a therapeutically effective amount of a pharmaceutical composition comprising ceftolozane sulfate and sodium chloride.

Non-limiting examples of bacterial infections that can be treated by the methods of the invention include infections caused by: aerobic and facultative gram-positive microorganisms (e.g., *Staphylococcus aureus, Enterococcus faecalis, Staphylococcus epidermidis, Streptococcus agalactiae, Streptococcus pneumonia, Streptococcus pyogenes, Viridans* group *streptococci*), aerobic and facultative gram-negative microorganisms (e.g., *Acinetobacter baumanii, Escherichia coli, Haemophilus influenza, Klebsiella pneumonia, Pseudomonas aeruginosa, Citrobacter koseri, Moraxella catarrhalis, Morganella morganii, Neisseria gonorrhoeae, Proteus mirabilis, Proteus vulgaris, Serratia marcescens, Providencia stuartii, Providencia rettgeri, Salmonella enterica*), gram-positive anaerobes (*Clostridium perfringens*), and gram-negative anaerobes (e.g., *Bacteroides fragilis* group (e.g., *B. fragilis, B. ovatus, B. thetaiotaomicron*, and *B. vulgates*), *Bacteroides distasonis, Prevotella melaninogenica*).

In certain embodiments of the methods described herein, bacterial infection is associated with one or more of the following conditions: complicated intra-abdominal infections, complicated urinary tract infections (cUTIs) and pneumonia (e.g., community-acquired, or nosocomial pneumonia). Community-acquired pneumonia (moderate severity only) can include infections caused by piperacillin-resistant, beta-lactamase producing strains of *Haemophilus influenza*. Nosocomial pneumonia (moderate to severe) caused by piperacillin-resistant, beta-lactamase producing strains of *Staphylococcus aureus* and by *Acinetobacter baumanii, Haemophilus influenzae, Klebsiella pneumoniae*, and *Pseudomonas aeruginosa*.

As used herein, "treating", "treat" or "treatment" describes the management and care of a patient for the purpose of combating a disease, condition, or disorder and includes the administration of a pharmaceutical composition of the present invention to alleviate the symptoms or complications of a disease, condition or disorder, or to reduce the extent of the disease, condition or disorder. The term "treat" can also include treatment of a cell in vitro or an animal model.

By a "therapeutically effective amount" of a compound of the invention is meant a sufficient amount of the compound to treat the disorder (e.g., bacterial infection). The specific therapeutically effective amount that is required for the treatment of any particular patient or organism (e.g., a mammal) will depend upon a variety of factors including the disorder being treated and the severity of the disorder; the activity of the specific compound or composition employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety). The therapeutically effective amount for a given situation can be readily determined by routine experimentation and is within the skill and judgment of the ordinary clinician.

As used herein, the term "ceftolozane active" refers to active portion of a salt form of ceftolozane in the free base form of ceftolozane.

As used herein, the term "tazobactam active" refers to the active portion of a salt form of tazobactam in the tazobactam free acid form.

As used herein, "1,000 mg of ceftolozane as ceftolozane active" refers to an amount of ceftolozane sulfate effective to provide 1,000 mg of ceftolozane active. The amount of sodium chloride per gram of ceftolozane activity in a pharmaceutical composition containing ceftolozane sulfate and sodium chloride can be calculated using the relevant molecular weights of ceftolozane, ceftolozane sulfate, sodium chloride and sodium. As used herein, "500 mg of tazobactam as tazobactam active" refers to an amount of tazobactam sodium or tazbactam arginine effective to provide 500 mg of tazobactam active.

As used herein, references to an amount of a substance as "% of the compound of . . . " or "% by HPLC" (unless otherwise indicated) refer to the % of a compound detected by high performance liquid chromatography (HPLC) according to the method of Example 2.

Illustrative Examples of Selected Embodiments of the Invention

EXAMPLE 1

Manufacturing Procedure of Bulk (Tray) Lyophilized Ceftolozane

There are four main steps in the manufacture of CXA-101 bulk drug product: dissolution, sterile filtration, bulk lyophilization, and packaging into Sterbags®. These four main steps are composed of a total of 20 minor steps. The CXA-101 bulk drug product manufacturing process is presented below.

I. Dissolution
1. The prescribed amount of water for injection ("WFI") is charged into the dissolution reactor.
2. A prescribed amount of citric acid is added.
3. The solution is cooled at 5° C. to 10° C.
4. A prescribed amount of CXA-101 drug substance is added to the solution.
5. A prescribed amount of L-arginine is slowly added to the solution.
6. A check for complete dissolution is performed. Solution pH is verified to be in the target range of 6.5 to 7.0.
7. A prescribed amount of sodium chloride is added to the solution.
8. A check for complete dissolution is performed. Solution pH is verified to be in the target range of 6.0 to 7.0. If the pH is out of this range adjust with either L-Arginine or citric acid.
9. WFI is added to bring the net weight to 124.4 kg and the solution is mixed well.
10. Samples are withdrawn for testing of final pH.

II. Sterile Filtration
11. The solution is passed through the filter (pore size 0.45 μm) followed by double filters (pore size 0.22 μm) onto a shelf on the Criofarma lyophilizer.
12. The line is washed with WFI.
13. The washing solution is passed from Step 12 through sterile filtration.

III. Bulk Lyophilization
14. The washing solution is loaded onto a separate shelf in the lyophilizer (and later discarded).
15. The solution is lyophilized until dry.
16. The product shelf is cooled to 20° C.±5° C.

IV. Packaging into Sterbags®
17. The lyophilized bulk drug product powder is milled.
18. The milled powder is sieved.
19. The sieved powder is blended for 30 minutes.
20. The powder is then discharged into Sterbags®

Prefiltration and Sterile-Filtration

Filtrate the compounded solution with a sterile tilter-set which consists of a 0.2 um polyvinylidene fluoride membrane filter (Durapore®, Millipore) and a 0.1 urn polyvinylidene fluoride membrane filter (Durapore®, Millipore) connected in tandem. Confirm the integrity of each filter before and after the filtration. Take approximately 100 mL of the filtrate in order to check bioburden.

Filter the prefiltered compounded solution through a sterile filter-set which consists of a 0.2 um polyvinylidene fluoride membrane filter and a 0.1 urn polyvinylidene fluoride membrane filter connected in tandem, and introduce the final filtrate into an aseptic room. Confirm the integrity of each filter before and after the filtration.

Processing of Vial, Stopper and Flip-Off Cap

Wash a sufficient quantity of 28 mL vials with water for injection and sterilize the washed vials by a dry-heat sterilizer. Then transfer the sterilized vials into a Grade A area located in an aseptic room.

Wash a sufficient quantity of stoppers with, water for injection. Sterilize and dry the washed stoppers by steam sterilizer. Then transfer the sterilized stoppers into a Grade A area located in an aseptic room.

Sterilize a sufficient quantity of flip-off caps by steam sterilizer. Then transfer the sterilized flip-off caps into a Grade A or B area located in an aseptic room.

Filling and Partially Stoppering

Adjust the fill weight of the filtered compounded solution to 11.37 g (corresponds to 10 mL of the compounded solution), then start filling operation. Check the filled weight in sufficient frequency and confirm it is in target range (11.37 g±1%, 11.26 to 11.43 g). When deviation from the control range (11.37 g±2%, 11.14 to 11.59 g) is occurred, re-adjust the filling weight.

Immediately after a vial is filled, partially stopper the vial with a sterilized stopper. Load the filled and partially stoppered vials onto the shelves of a lyophilizer aseptically.

Lyophilization to Crimping, Visual Inspection, Labeling and Packaging

After all filled and partially stoppered vials are loaded into a lyophilizer, start the lyophilization program shown in FIG. 2. Freeze the loaded vials at −40° C. and keep until all vials freeze. Forward the program to primary drying step (shelf temperature; −20° C., chamber pressure; 100 to 150 mTorr). Primary drying time should be determined by monitoring the product temperature. Forward the program to secondary drying step (shelf temperature; 30° C., chamber pressure; not more than 10 mTorr) after completion of the primary drying step. After all vials are dried completely, return the chamber pressure to atmospheric pressure with sterilized nitrogen. Then stopper vials completely.

Unload the lyophilized vials from the chamber and crimp with sterilized flip-off caps.

Subject all crimped vials to visual inspection and label and package all passed vials.

EXAMPLE 2

Analytical HPLC Method

A. Operative Conditions

| Column | Develosil ODS-UG-5; 5 μm, 250 × 4.6 mm (Nomura Chemical, Japan) | | |
|---|---|---|---|
| Mobile phase | Sodium Perchlorate Buffer Solution (PH 2.5)/CH₃CN 90:10 (v/v) | | |
| Flow rate | 1.0 mL/min | | |
| Wavelength | 254 nm | | |
| Injection volume | 10 μL | | |
| Oven Temperature | 45° C. | | |
| Run Time | 85 minutes | | |
| | Time (min) | A % | B % |
| Gradient Profile: | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

B. Mobile Phase Preparation.

Sodium Perchlorate Buffer Solution was made by dissolving 14.05 g of sodium perchlorate Monohydrate in 1000.0 mL of water followed by adjusting pH to 2.5 with diluted perchloric acid (1 in 20).

Mobile Phase was then made by mixing Sodium Perchlorate Buffer Solution (pH 2.5) and acetonitrile in the ratio 90:10 (v/v).

Sodium Acetate Buffer Solution pH 5.5 (Diluent) was made by dissolving 1.36 g of sodium acetate trihydrate in 1000.0 mL of water followed by adjusting to pH 5.5 with diluted acetic acid (1 in 10).

C. Sample Preparation.

Sample solution: dissolve 20.0 mg, exactly weighed, of Sample, in 20.0 mL of water (Prepare just before injection into HPLC system).

System Suitability Solution (1%): take 1.0 mL of the Sample Solution (use first sample if more are present) and transfer into a 100.0 mL volumetric flask, dilute with water to volume and mix.

D. HPLC Analysis Procedure

Figure 1A:
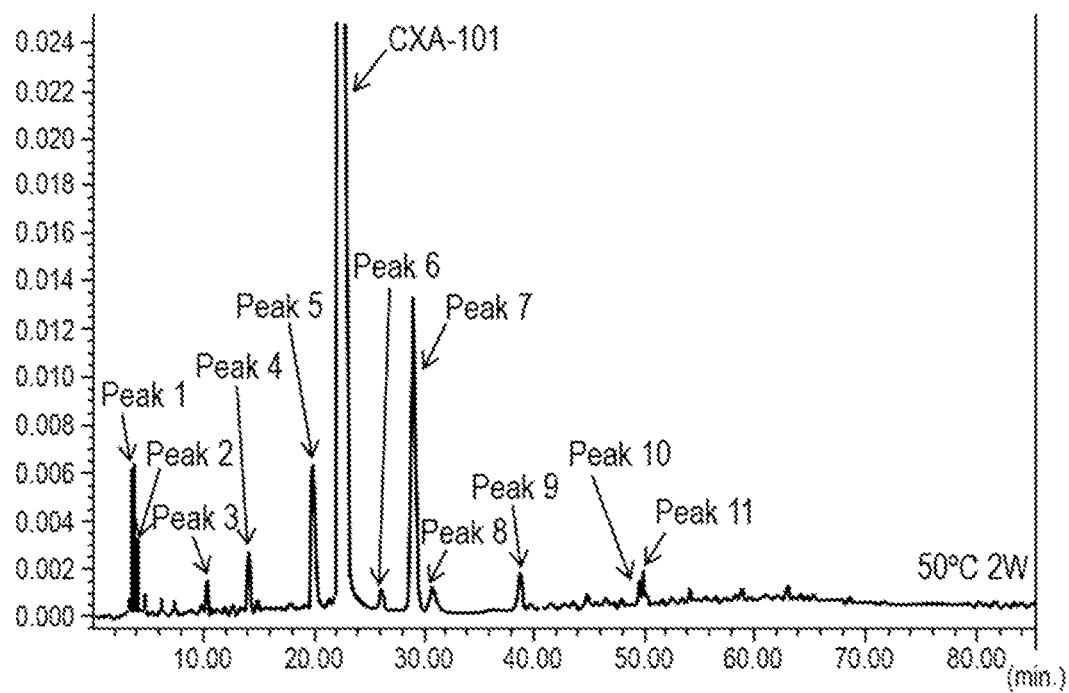
FIGS. 1A and 1B are chromatograms of CXA-101 ceftolozane drug substance obtained from the lyophilization process
Figure 1B:
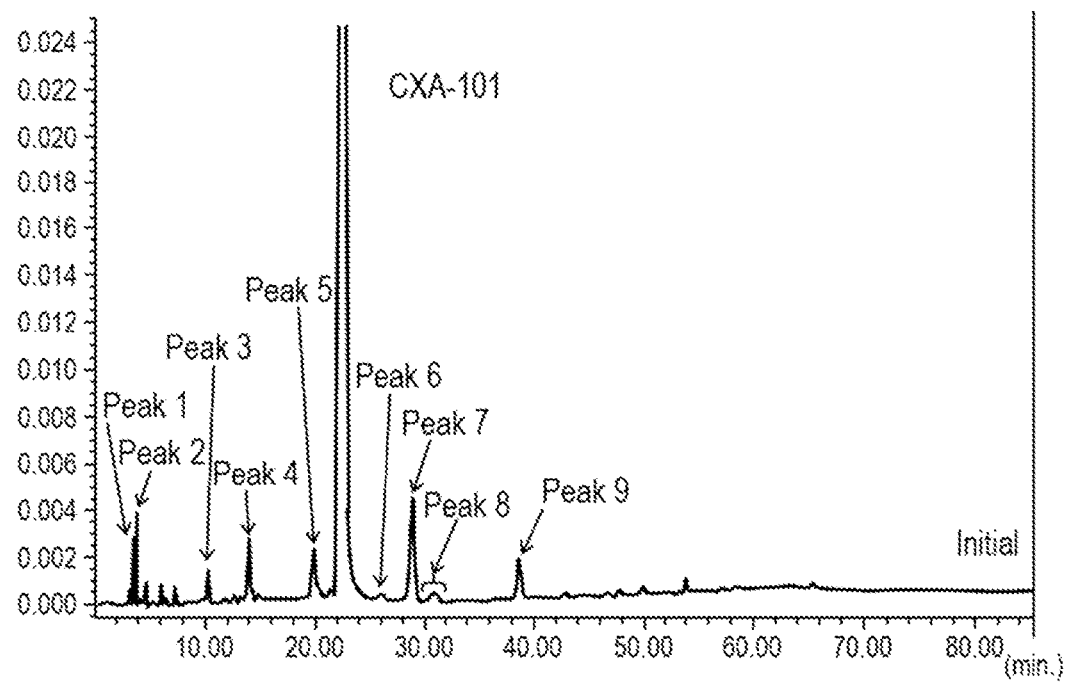

1. Inject Blank (water)
2. Inject System Suitability Solution and check for tailing factor and theoretical plate number for CXA-101 peak:
   The tailing factor must not be greater than 1.5
   Theoretical plates number must not be less than 10000
3. Inject Sample Solution
4. Inject System Suitability Solution and check for tailing factor and theoretical plate number for CXA-101 peak.
   The tailing factor must not be greater than 1.5
   Theoretical plates number must not be less than 10000
5. Identify the peaks of Related Substances in the Sample chromatogram based on the reference chromatogram reported in FIGS. 1A and 1B or, alternatively, on the basis of the RRT values reported in Table 1 (FIG. 3)

E. Calculations

I. Report for each related substance its amount as expressed by area percent.

$$C_i = \frac{A_i \times 100}{A_t + \sum A_i}$$

wherein:

$C_i$=Amount of related substance i in the Sample, area %

$A_i$=Peak area of related substance i in the Sample chromatogram $A_t$=Area of CXA-101 peak in the Sample chromatogram $A_t + \sum A_i$=Total peaks area in the Sample chromatogram Consider as any Unspecified Impurity, each peak in the chromatogram except CXA-101, peaks from 1 to 11 and every peak present in the blank chromatogram and report the largest.

II. Report the total impurities content as expressed by the following formula:

$$C_T = \frac{A_i \times 100}{A_t + \sum A_i}$$

wherein:

$C_T$=total impurities content in the Sample, area %

$A_t$=area of CXA-101 peak in the sample chromatogram $\sum A_i$=total peak areas of impurities in the sample chromatogram

EXAMPLE 3

Manufacturing of Combination Product (Tazobactam and Ceftolozane) Comprising a Compound of Formula (III) by Co-Lyophilization Compositions comprising the compound of formula (III) were prepared by the process shown in FIG. 4A by (a) forming an aqueous solution comprising the components in Table 2 (FIG. 4B), and (b) lyophilizing the aqueous solution. Sodium content was approximately 78 mg/g of tazobactam in drug product after lyophilization. Water was removed during the lyophilization process and is controlled at no more than 4% by HPLC.

EXAMPLE 4

Manufacturing of Combination Product (Tazobactam and CXA-101) without HPLC-Detectable Amounts of the Compound of Formula (III) by Blending Sterile Dry Blending of Bulk Lyophilized Ceftolozane and Bulk Lyophilized Tazobactam The CXA-101 produced by Example 1 is blended with lyophilized tazobactam. A low energy drum blender that agitates the material by tumbling and also moving the bed up and down is used. A representative process of blending is described according to the table in FIG. 5. The table in FIG. 5 shows in-process testing of blending samples of bulk drug product at five places. For CXA-101/tazobactam for injection, the blender was charged with 23.4 kg of CXA-101 bulk product, and 5.4 kg of tazobactam bulk product. Both the CXA-101 and tazobactam were individually lyophilized beforehand. The material was blended for 180 minutes. In-process tests of content assay for both CXA-101 and tazobactam were performed to assess the homogeneity using the samples of blend materials taken from three places. The RSD for each of CXA-101 and tazobactam content assay was no greater than 2% and the RSD for the ratio of CXA-101/tazobactam was no greater than 2.2%. (See Table 3 in FIG. 5).

EXAMPLE 5

Co-Lyophilization of Ceftolozane and Tazobactam Produces the Compound of Formula (III) (RRT 1.22)

The Co-Lyophilized Combo Drug Product was prepared as described above in Example 3. The formulation composition of the Co-Lyophilized Combo drug product is shown in FIG. 6 (Table 4). This sample was maintained at 25° C./RH=60% and 40° C./RH=75% after one month (T1) and three months (T2). Samples were analyzed using a HPLC method as described in Example 2. The data for analysis of the samples by HPLC is shown in the tables in FIG. 7A (Table 5: Stability data of Co-Lyo Combo Drug Product at 25° C.) and FIG. 7B (Table 6: Stability data Co-Lyo Combo Drug Product at 40° C.). The presence of the compound of Formula (III) was identified has having a retention time of about 1.22 as measured by HPLC (see Example 2). RRT=1.22 was observed in co-lyophilized drug product. The compound of formula (III) is believed to be formed by a reaction between ceftolozane and formylacetic acid, which was a degradation product of tazobactam. The amount of the compound of formula (III) in a composition comprising ceftolozane and tazobactam can be increased over time at 25° C. and at 40° C.

EXAMPLE 6

Assessment of Blend Combination Drug Product

A. Preparation of Blend Combination Drug Product

The blend drug product was prepared, as described above in Example 4, on lab scale by use of a small blender. The composition of the blend drug product is shown in Table 7, FIG. 8. The CXA-101 was obtained by lyophilization of ceftolozane sulfate in the absence of tazobactam, and the tazobactam sodium material was obtained by lyophilization of tazobactam prior to blending of the ceftolozane and tazobactam components.

B. Stress Test

This sample was put into stability study. The following Tables 8 (FIG. 9A) and 9 (FIG. 9B) are representative examples that summarizes the results at 25° C./RH=60% and 40° C./RH=75% after one month (T1) and three months (T2). Samples were analyzed using a HPLC method as described in Example2.

C. Conclusion

The data at both 25° C. and at 40° C. have shown that the blending process inhibits formation of amounts of the impurity RRT=1.22 to below the detection limit of the HPLC method of Example 2.

EXAMPLE 7

Preferred Pharmaceutical Composition Comprising Ceftolozane and Tazobactam

Pharmaceutical compositions comprising ceftolozane and tazobactam with less than 0.15% (measured by HPLC according to Example 2) of the compound of formula (III) can be obtained as described herein.

TABLE 10

Excipients Used in Ceftolozane composition

| Component | Function | Amount, mg/Vial | Concentration in Infusion Solution, % | Rationale for Inclusion | Inactive Ingredients Database (IID) Range |
| --- | --- | --- | --- | --- | --- |
| Citric acid | Chelating agent | 21 | 0.02 | Used to prevent discoloration and degradation | 0.0025 to 50% |
| Sodium Chloride | Stabilizing agent | 487 | 0.49 | Used as a stabilizing agent for ceftolozane sulfate | 0.187 to 45% |
| L-arginine | Alkalizing agent | 600[i) Q.S. for pH adjustment | 0.60 | Used to adjust ceftolozane solution pH | 0.29 to 88% |

[i)L-arginine is added as needed to achieve pH 6.5 ± 0.5; 600 mg per vial is considered a representative total amount.

TABLE 11

Unit Compositions of Ceftolozane/Tazobactam for Injection, 1000 mg/500 mg

| Component | | Function | Nominal Composition mg per Vial |
| --- | --- | --- | --- |
| Ceftolozane composition[1) | Ceftolozane Sulfate | Active | 1147 |

TABLE 11-continued

Unit Compositions of Ceftolozane/Tazobactam for Injection,
1000 mg/500 mg

| Component | Function | Nominal Composition mg per Vial |
|---|---|---|
| Citric Acid, Anhydrous | Chelating Agent | 21 |
| Sodium Chloride | Stabilizing Agent | 487 |
| L-Arginine | Alkalizing Agent | 600[2] Q.S. for pH adjustment |
| Tazobactam Sodium[3] | Active | 537 |
| Nitrogen | Processing Aid[4] | Q.S. |
| Total Weight | | 2792 |

[1] Actual amount of ceftolozane composition will vary based on the measured potency. Ceftolozane sulfate, 1147 mg, corresponds to 1000 mg ceftolozane free base.
[2] L-arginine is added as needed to achieve pH 6.5 ± 0.5; 600 mg per vial is considered a representative total amount.
[3] Actual weight of tazobactam sodium will vary based on the measured potency. Tazobactam sodium 537 mg, corresponds to 500 mg tazobactam free acid
4) Nitrogen blanket is applied after powders are dispensed to the vial and prior to insertion of stopper.

A first aqueous solution comprising the ingredients in the Ceftolozane composition in Table 11 is lyophilized in the absence of tazobactam to provide the lyophilized Ceftolozane composition. The first aqueous solution comprises ceftolozane sulfate and the specific excipients in the preferred compositions, in an amount per unit dosage form provided by the quantities and functions as provided in Table 10. All excipients are compendial and typical for sterile pharmaceutical dosage forms, requiring no additional treatment prior to use in the formulation. The excipients are used in levels within the range established in other FDA approved products as described in the Inactive Ingredients Database (IID). A second solution comprising tazobactam acid and sodium bicarbonate is lyophilized in the absence of ceftolozane to obtain the Tazobactam Sodium Composition in Table 11. Subsequently, the lyophilized Tazobactam Sodium Composition is dry blended with the lyophilized Ceftolozane composition comprising tazobactam sodium and ceftolozane sulfate in a weight ratio providing 500 mg of tazobactam acid equivalent per 1,000 mg of ceftolozane active equivalent.

What is claimed is:

1. A method of treating an infection selected from the group consisting of a complicated intra-abdominal infection and a complicated urinary tract infection in a patient comprising administering to the patient a therapeutically effective amount of a pharmaceutical composition comprising (a) ceftolozane lyophilized in the absence of tazobactam and (b) a tazobactam composition, in a ratio of 1,000 mg ceftolozane active per 500 mg of tazobactam active.

2. The method of claim 1, wherein the infection is a complicated urinary tract infection.

3. The method of claim 1, wherein the pharmaceutical composition is intravenously administered to the patient as an infusion after combining the ceftolozane lyophilized in the absence of tazobactam and the tazobactam composition with a pharmaceutically acceptable carrier.

4. The method of claim 1, wherein the pharmaceutical composition comprises an amount of a pharmaceutically acceptable salt of ceftolozane providing a total of 1,000 mg of ceftolozane active, blended with the tazobactam composition to form the pharmaceutical composition.

5. The method of claim 1, wherein the tazobactam in the tazobactam composition is tazobactam sodium.

6. The method of claim 1, wherein the tazobactam in the tazobactam composition is a crystalline tazobactam.

7. The method of claim 1, wherein the ceftolozane is ceftolozane sulfate.

8. The method of claim 1, wherein the pharmaceutical composition does not contain a compound of formula (III)

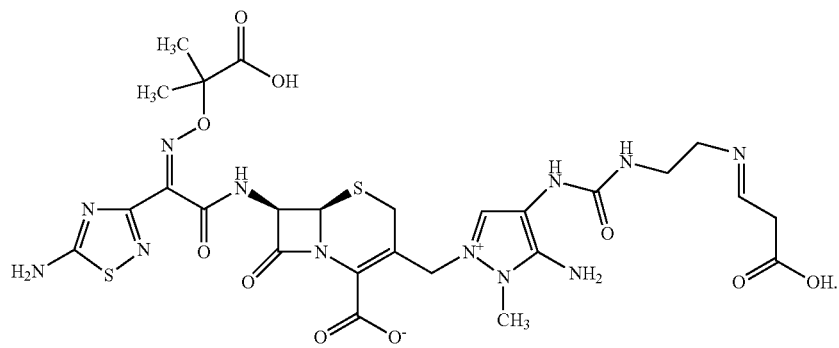

(III)

9. A method of treating an infection in a patient selected from the group consisting of a complicated intra-abdominal infection and a complicated urinary tract infection, the method comprising intravenously administering to the patient a therapeutically effective amount of ceftolozane obtained by lyophilizing a solution comprising ceftolozane without tazobactam to obtain a ceftolozane composition, and tazobactam in a ratio of 1,000 mg ceftolozane active per 500 mg of tazobactam active.

10. The method of claim 9, wherein the ceftolozane and the tazobactam are administered in a pharmaceutical composition comprising an amount of a pharmaceutically acceptable salt of ceftolozane providing a total of 1,000 mg of ceftolozane active.

11. The method of claim 10, wherein the pharmaceutical composition is obtained by a process comprising the step of combining tazobactam lyophilized in the absence of ceftolozane with the lyophilized ceftolozane composition.

12. The method of claim 9, wherein the tazobactam is tazobactam sodium.

13. The method of claim 9, wherein the tazobactam is a crystalline tazobactam.

14. The method of claim 9, wherein the ceftolozane is ceftolozane sulfate.

15. The method of claim 10, wherein the pharmaceutical composition does not contain a compound of formula (III)

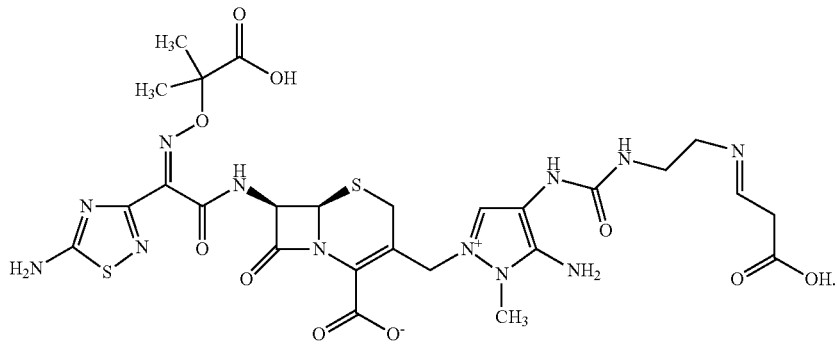

(III)

16. The method of claim 10, wherein the ceftolozane and the tazobactam are lyophilized in separate solutions prior to forming the pharmaceutical composition.

17. The method of claim 9, wherein the ceftolozane composition is obtained by dissolving a compound of formula (I):

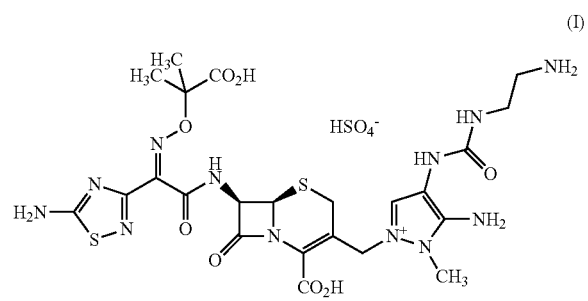 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

(I)

in the solution, adjusting the pH of the solution to about 5-7 prior to lyophilization, and lyophilizing the solution to obtain the lyophilized ceftolozane composition.

18. A method of treating an infection selected from the group consisting of a complicated intra-abdominal infection and a complicated urinary tract infection in a patient comprising:

dissolving in a pharmaceutically acceptable carrier a composition comprising tazobactam and ceftolozane prepared in the absence of tazobactam to obtain a pharmaceutical composition comprising ceftolozane active and tazobactam active in a 2:1 weight ratio; and administering to the patient a therapeutically effective amount of the pharmaceutical composition.

19. The method of claim 18, wherein the infection is a complicated urinary tract infection.

20. The method of claim 18, wherein the pharmaceutical composition is intravenously administered to the patient as an infusion.

21. The method of claim 20, wherein the pharmaceutical composition comprises an amount of a pharmaceutically acceptable salt of ceftolozane providing a total of 1,000 mg of ceftolozane active.

22. The method of claim 18, wherein the ceftolozane is obtained by a process comprising the step of lyophilizing a solution comprising ceftolozane sulfate in the absence of tazobactam.

23. The method of claim 20, wherein the pharmaceutical composition is obtained by a process comprising the step of combining tazobactam with the lyophilized ceftolozane composition.

24. The method of claim 18, wherein the tazobactam is tazobactam sodium.

25. The method of claim 18, wherein the pharmaceutical composition does not contain a compound of formula (III)

(III)

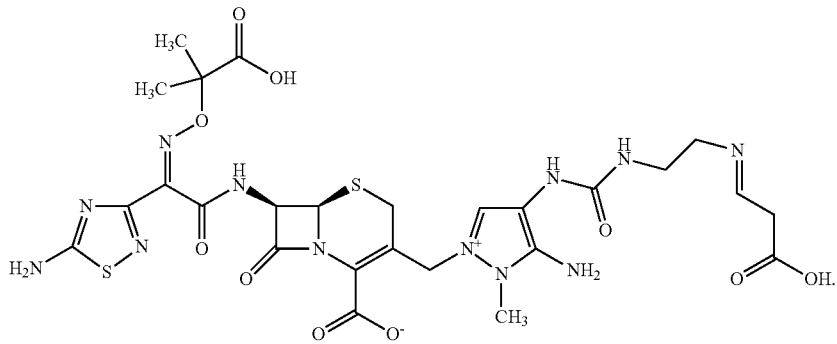

26. The method of claim 18, wherein the ceftolozane and the tazobactam are lyophilized in separate solutions prior to administering to the patient.

27. The method of claim 18, wherein the ceftolozane is lyophilized in the absence of tazobactam and is prepared by lyophilizing a solution of ceftolozane of formula (I) in the absence of tazobactam, adjusted to a pH to about 5-7 prior to lyophilization:

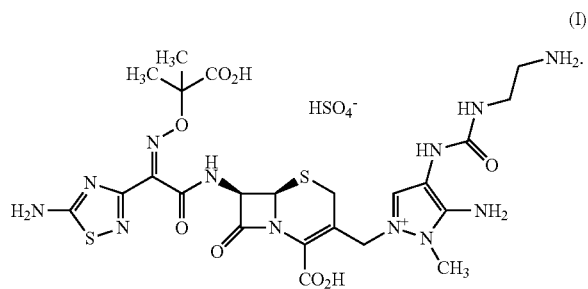 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]
(I)

28. A method of treating an infection selected from the group consisting of a complicated intra-abdominal infection and a complicated urinary tract infection in a patient comprising administering to the patient a therapeutically effective amount of a pharmaceutical composition comprising:
 (a) tazobactam or a pharmaceutically acceptable salt thereof and
 (b) a lyophilized ceftolozane composition, wherein prior to lyophilization the ceftolozane composition does not contain tazobactam or salts thereof.

29. The method of claim 28, wherein the pharmaceutical composition comprises the ceftolozane and the tazobactam in a weight ratio of about 2:1 between the ceftolozane active and the tazobactam active.

30. The method of claim 29, wherein the lyophilized ceftolozane is lyophilized in a solution comprising ceftolozane of formula (I) in the absence of tazobactam:

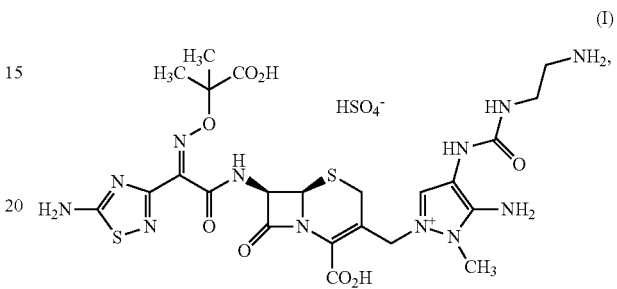
(I)

adjusted to a pH of about 5-7 prior to lyophilization.

* * * * *